US 10,791,595 B2

(12) United States Patent
Kuboi et al.

(10) Patent No.: US 10,791,595 B2
(45) Date of Patent: Sep. 29, 2020

(54) ILLUMINATING DEVICE

(71) Applicant: OLYMPUS CORPORATION, Tokyo (JP)

(72) Inventors: Toru Kuboi, Machida (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/506,336

(22) Filed: Jul. 9, 2019

(65) Prior Publication Data

US 2020/0008280 A1 Jan. 2, 2020

Related U.S. Application Data

(63) Continuation of application No. PCT/JP2017/000668, filed on Jan. 11, 2017.

(51) Int. Cl.
*H05B 45/10* (2020.01)
*A61B 1/06* (2006.01)
*G01K 7/00* (2006.01)

(52) U.S. Cl.
CPC ........... *H05B 45/10* (2020.01); *A61B 1/0661* (2013.01); *G01K 7/00* (2013.01)

(58) Field of Classification Search
CPC ......... H05B 45/10; A61B 1/0661; G01K 7/00
(Continued)

(56) References Cited

U.S. PATENT DOCUMENTS 8,214,084 B2 * 7/2012 Ivey .......................... F24F 11/62
700/275
8,339,069 B2 * 12/2012 Chemel ................ H05B 47/155
315/297

(Continued)

FOREIGN PATENT DOCUMENTS

JP          S61-79285 A      4/1986
JP       2000-294871 A     10/2000
(Continued)

OTHER PUBLICATIONS

International Search Report dated Feb. 28 2017 issued in PCT/JP2017/000668.

(Continued)

*Primary Examiner* — Bryon T Gyllstrom
(74) *Attorney, Agent, or Firm* — Scully, Scott, Murphy & Presser, P.C.

(57) ABSTRACT

An illuminating device includes: a semiconductor light source; a temperature control unit disposed on the light source for controlling a temperature of the light source to a desired temperature; a dew condensation determination unit for determining whether dew condensation may occur based on at least a temperature associated with the illuminating device and an ambient environment condition of the illuminating device; and a temperature control mode selection control unit for selecting, as a temperature control mode of the temperature control unit, a dew condensation suppression mode in which the temperature control unit has a temperature higher than a predetermined temperature and equal to or less than an upper limit of a usable temperature of the light source, based on priority items of operational control of the illuminating device and characteristics of the light source, to temperature-control the temperature control (Continued)

unit, when the determination unit determines that dew condensation may occur.

20 Claims, 18 Drawing Sheets

(58) Field of Classification Search
USPC .......................................................... 362/552
See application file for complete search history.

(56) References Cited

U.S. PATENT DOCUMENTS

| | | | | |
|---|---|---|---|---|
| 8,368,321 | B2* | 2/2013 | Chemel | H05B 47/155 |
| | | | | 315/294 |
| 8,373,362 | B2* | 2/2013 | Chemel | H05B 47/155 |
| | | | | 315/297 |
| 8,536,802 | B2* | 9/2013 | Chemel | H05B 47/155 |
| | | | | 315/307 |
| 8,605,763 | B2* | 12/2013 | Castillo | H05B 45/10 |
| | | | | 372/34 |
| 8,610,377 | B2* | 12/2013 | Chemel | H05B 47/155 |
| | | | | 315/308 |
| 2004/0160199 | A1* | 8/2004 | Morgan | F21S 4/20 |
| | | | | 315/312 |
| 2009/0021955 | A1* | 1/2009 | Kuang | H05B 45/10 |
| | | | | 362/479 |
| 2012/0105253 | A1* | 5/2012 | Lillis | G09G 3/32 |
| | | | | 340/945 |
| 2012/0235579 | A1* | 9/2012 | Chemel | H05B 47/19 |
| | | | | 315/152 |
| 2015/0035437 | A1* | 2/2015 | Panopoulos | H05B 47/19 |
| | | | | 315/112 |
| 2015/0155330 | A1 | 6/2015 | Oh et al. | |
| 2015/0264766 | A1* | 9/2015 | Takatsu | H05B 45/10 |
| | | | | 315/187 |

FOREIGN PATENT DOCUMENTS

| | | |
|---|---|---|
| JP | 2005-317841 A | 11/2005 |
| JP | 2006-304847 A | 11/2006 |
| JP | 2010-113986 A | 5/2010 |
| JP | 2014-187330 A | 10/2014 |
| JP | 2015-520518 A | 7/2015 |
| WO | WO 2016/027717 A1 | 2/2016 |

OTHER PUBLICATIONS

English translation of International Preliminary Report on Patentability dated Jul. 25, 2019, together with the Written Opinion received in related International Application No. PCT/JP2017/000668.

* cited by examiner

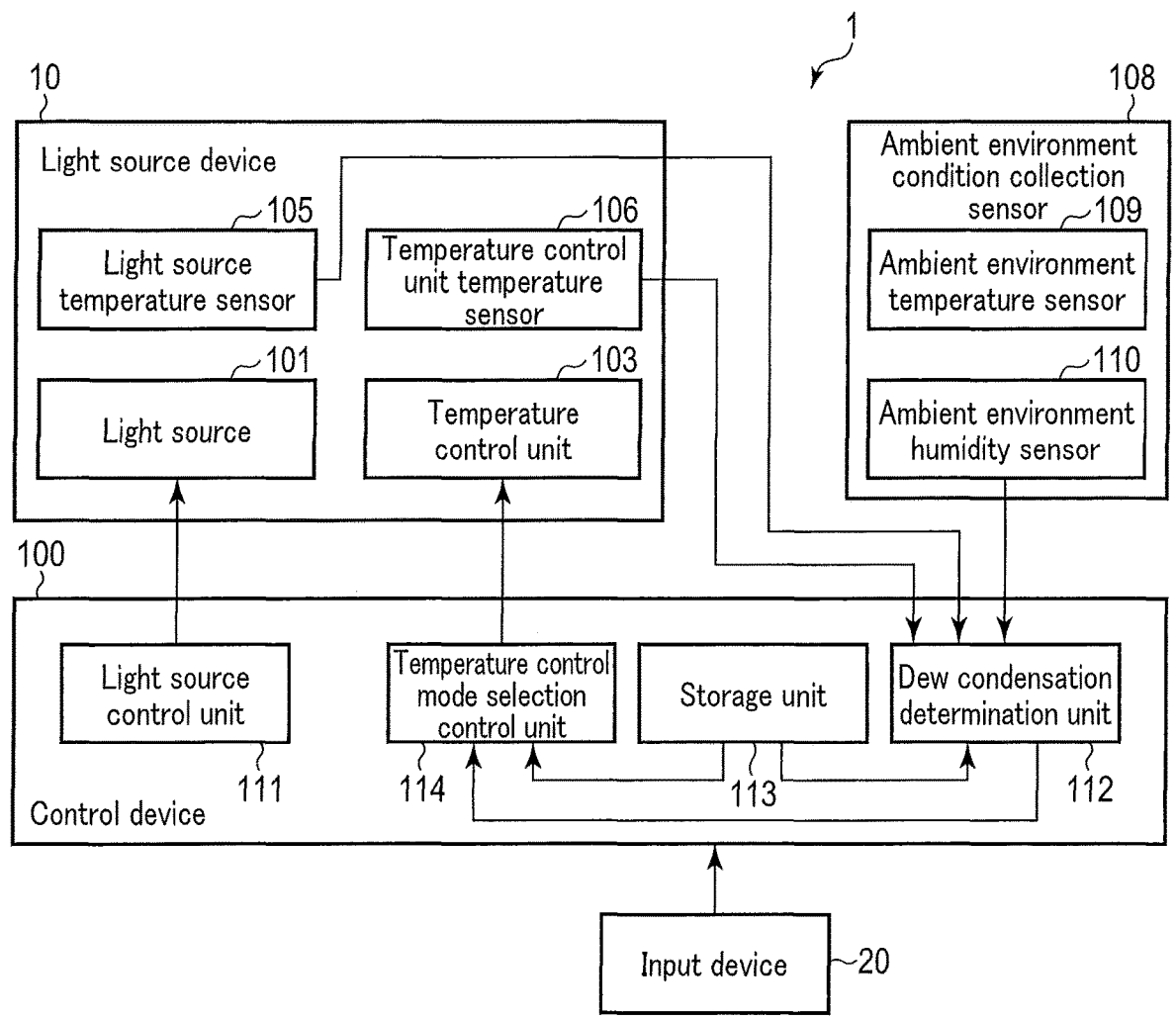
F I G. 2

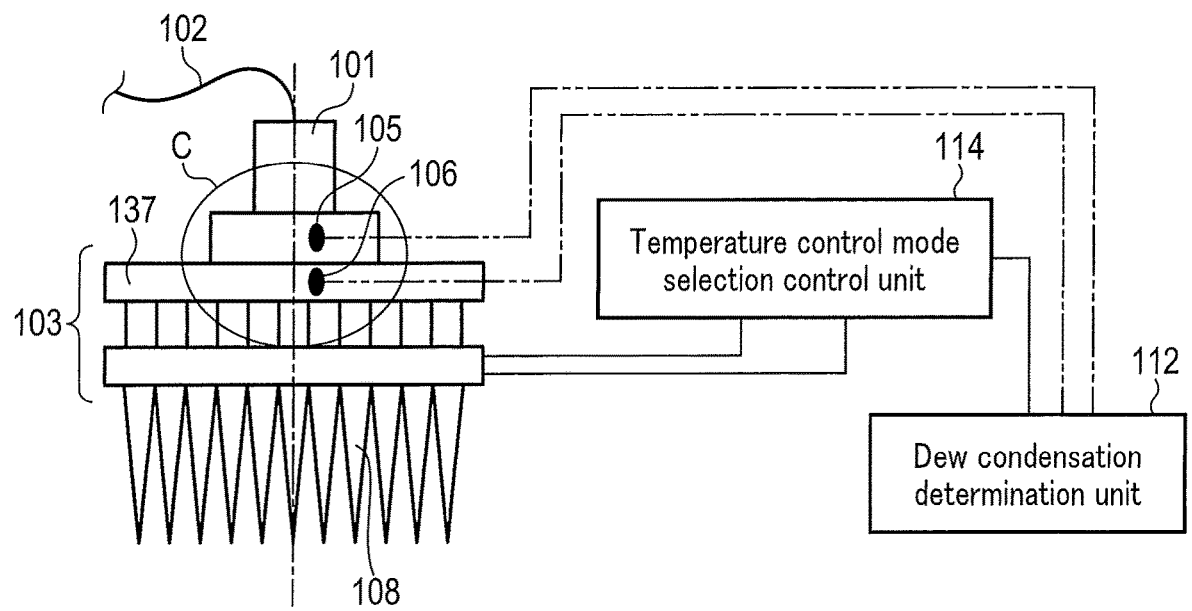
F I G. 3
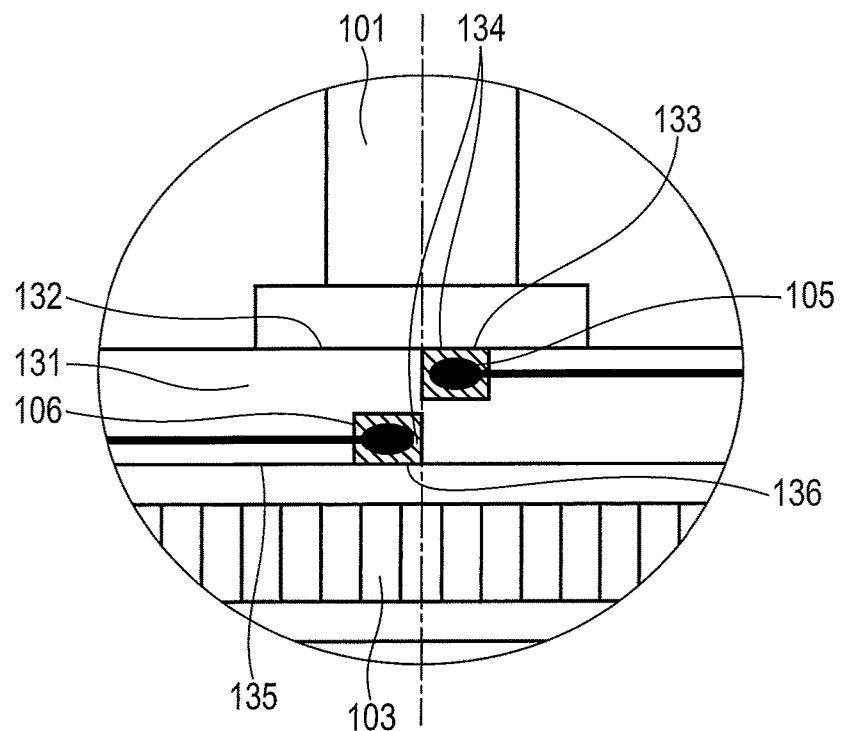
F I G. 4

FIG. 5

| Priority item setting | Light source setting | | | | | Selection timing | | | | |
|---|---|---|---|---|---|---|---|---|---|---|
| | | | | | | Always | Outside air | Rewriting | Cumulative time | Life exceeded |
| Light source life setting ☒ | R ☐ | G ☒ | B ☒ | V ☐ | A ☐ | /// | /// | /// | /// | /// |
| | R ☐ | G ☒ | B ☒ | V ☐ | A ☐ | /// | /// | /// | /// | /// |
| Special light observation setting ☒ | R ☒ | G ☒ | B ☒ | V ☐ | A ☐ | /// | /// | /// | /// | /// |
| | R ☒ | G ☒ | B ☒ | V ☐ | A ☐ | /// | /// | /// | /// | /// |
| All-color dew condensation suppression setting ☐ | /// | /// | /// | /// | /// | ☐ | ☐ | ☐ | ☐ | ☐ |
| | R ☒ | G ☒ | B ☒ | V ☒ | A ☒ | ☐ | ☐ | ☐ | ☐ | ☐ |
| All-color dew condensation suppression disable setting ☐ | R ☐ | G ☐ | B ☐ | V ☐ | A ☐ | ☐ | ☐ | ☐ | ☐ | ☐ |
| New light source setting ☐ | R ☐ | G ☐ | B ☐ | V ☐ | A ☐ | ☐ | ☐ | ☐ | ☐ | ☐ |
| | R ☒ | G ☐ | B ☐ | V ☐ | A ☐ | | | | | |
| Special use setting ☐ | R ☐ | G ☐ | B ☐ | V ☐ | A ☒ | | | | | |

| Priority item setting | | Light source setting | | | | | Selection timing | | | | |
|---|---|---|---|---|---|---|---|---|---|---|---|
| | | R | G | B | V | A | Always | Outside air | Rewriting | Cumulative time | Life exceeded |
| Light source life setting ☑ | R | | | | | | ☐ | | ☐ | ☐ | ☐ |
| | G | ☑ | | | | | ☐ | ☑ | ☐ | ☐ | ☐ |
| | B | ☑ | | | | | ☐ | ☑ | ☐ | ☐ | ☐ |
| | V | ☐ | | | | | ☐ | ☐ | ☐ | ☐ | ☐ |
| | A | ☐ | | | | | ☐ | ☐ | ☐ | ☐ | ☐ |
| Special light observation setting ☑ | R | ☑ | | | | | ☐ | ☑ | ☐ | ☐ | ☐ |
| | G | ☑ | | | | | ☐ | ☑ | ☐ | ☐ | ☐ |
| | B | ☑ | | | | | ☐ | ☑ | ☐ | ☐ | ☐ |
| | V | ☐ | | | | | ☐ | ☐ | ☐ | ☐ | ☐ |
| | A | ☐ | | | | | ☐ | ☐ | ☐ | ☐ | ☐ |
| All-color dew condensation suppression setting | R | G | B | V | A | | | | | | |

FIG. 7

| Priority item setting | | Light source setting | | | | | | Selection timing | | | | |
|---|---|---|---|---|---|---|---|---|---|---|---|---|
| | | R | G | B | V | A | | Always | Outside air | Rewriting | Cumulative time | Life exceeded |
| Light source life setting ☒ | R | ☐ | | | | | | ☐ | ☐ | ☐ | ☐ | ☐ |
| | G | ☒ | | | | | | ☐ | ☐ | ☒ | ☐ | ☐ |
| | B | ☒ | | | | | | ☐ | ☐ | ☒ | ☐ | ☐ |
| | V | ☐ | | | | | | ☐ | ☐ | ☐ | ☐ | ☐ |
| | A | ☐ | | | | | | ☐ | ☐ | ☐ | ☐ | ☐ |
| Special light observation setting ☒ | R | ☒ | | | | | | ☐ | ☐ | ☒ | ☐ | ☐ |
| | G | ☒ | | | | | | ☐ | ☐ | ☒ | ☐ | ☐ |
| | B | ☒ | | | | | | ☐ | ☐ | ☒ | ☐ | ☐ |
| | V | ☐ | | | | | | ☐ | ☐ | ☐ | ☐ | ☐ |
| | A | ☐ | | | | | | ☐ | ☐ | ☐ | | |
| All-color dew condensation suppression setting | R | ☐ | G | B | V | A | | | | | | |

FIG. 10

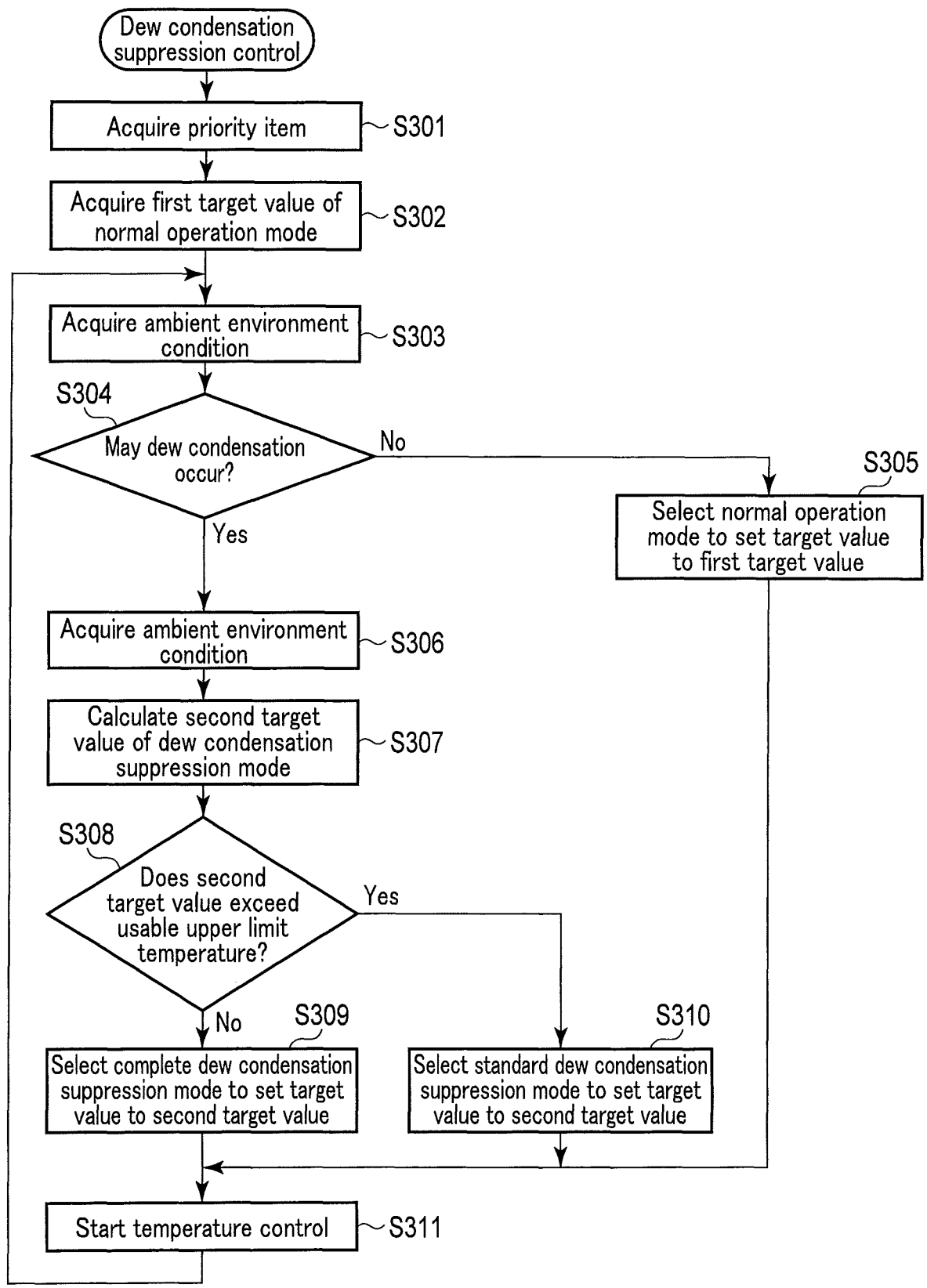
F I G. 11

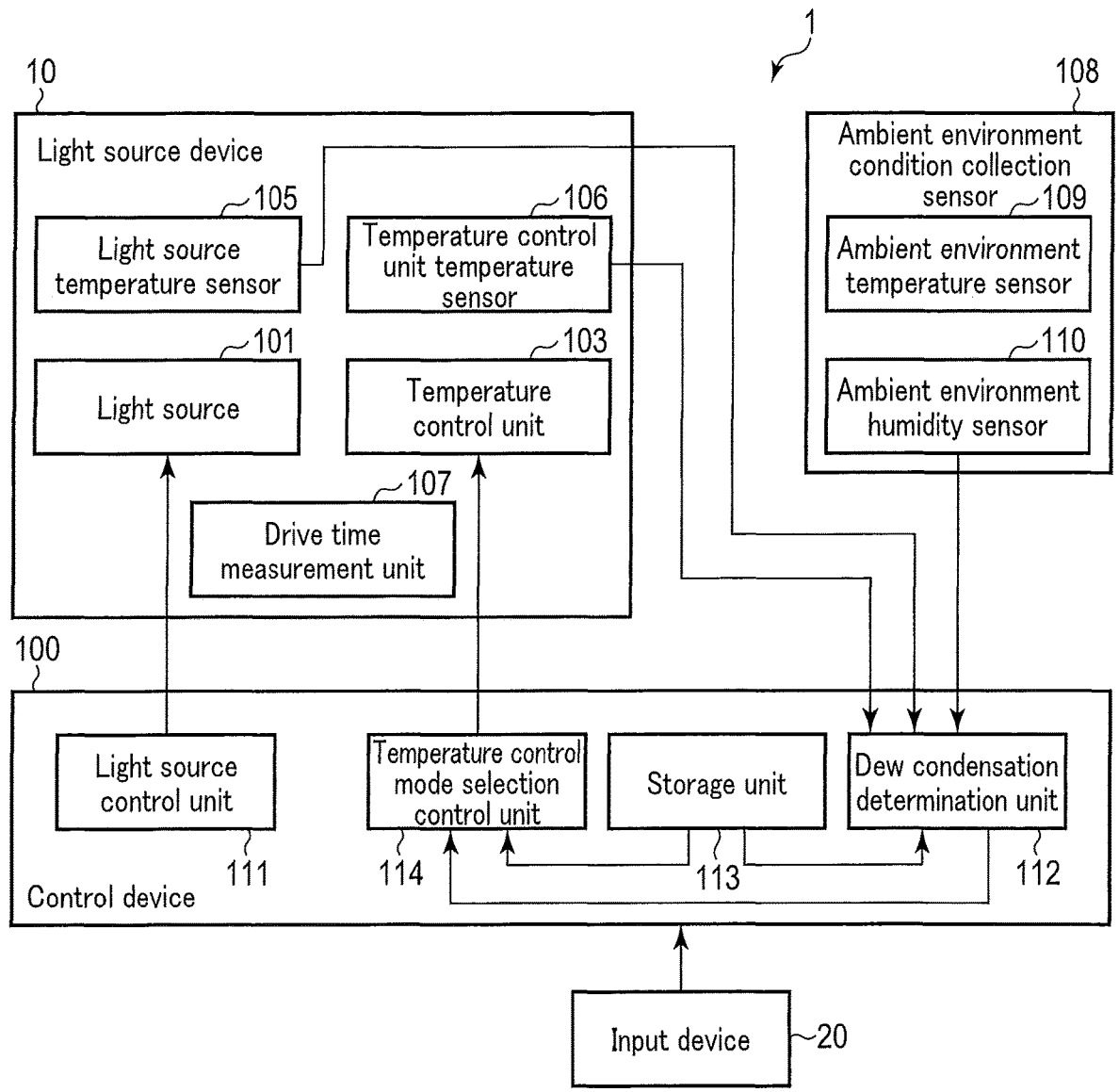
F I G. 13

| Priority item setting | Light source life setting | Light source setting | | | | | | | Selection timing | | | | |
|---|---|---|---|---|---|---|---|---|---|---|---|---|---|
| | | R | G | B | V | A | | Always | Outside air | Rewriting | Cumulative time | Life exceeded |
| | ☑ | ☐ | ☑ | ☑ | ☐ | ☐ | | ☐ | ☐ | ☐ | ☐ | ☐ |
| | | | | | | | | ☑ | ☐ | ☐ | ☑ | ☐ |
| | | | | | | | | ☑ | ☐ | ☐ | ☑ | ☐ |
| | | | | | | | | ☐ | ☐ | ☐ | ☐ | ☐ |
| | | | | | | | | ☐ | ☐ | ☐ | ☐ | ☐ |

| Priority item setting | Light source setting | | Selection timing | | | | |
|---|---|---|---|---|---|---|---|
| | | | Always | Outside air | Rewriting | Cumulative time | Life exceeded |
| Light source life setting ☒ | R | ☐ | ☐ | ☐ | ☐ | ☐ | ☐ |
| | G | ☒ | ☒ | ☐ | ☐ | ☐ | ☒ |
| | B | ☒ | ☒ | ☐ | ☐ | ☐ | ☒ |
| | V | ☐ | ☐ | ☐ | ☐ | ☐ | ☐ |
| | A | ☐ | ☐ | ☐ | ☐ | ☐ | ☐ |

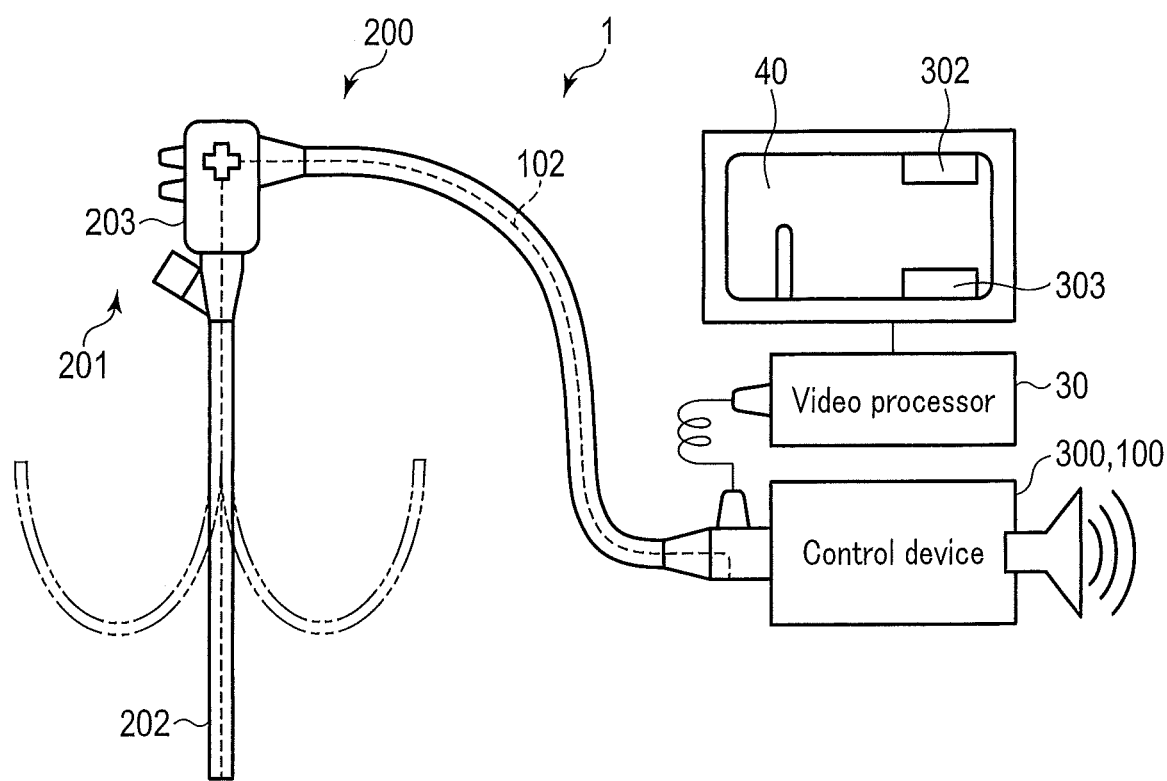
F I G. 18

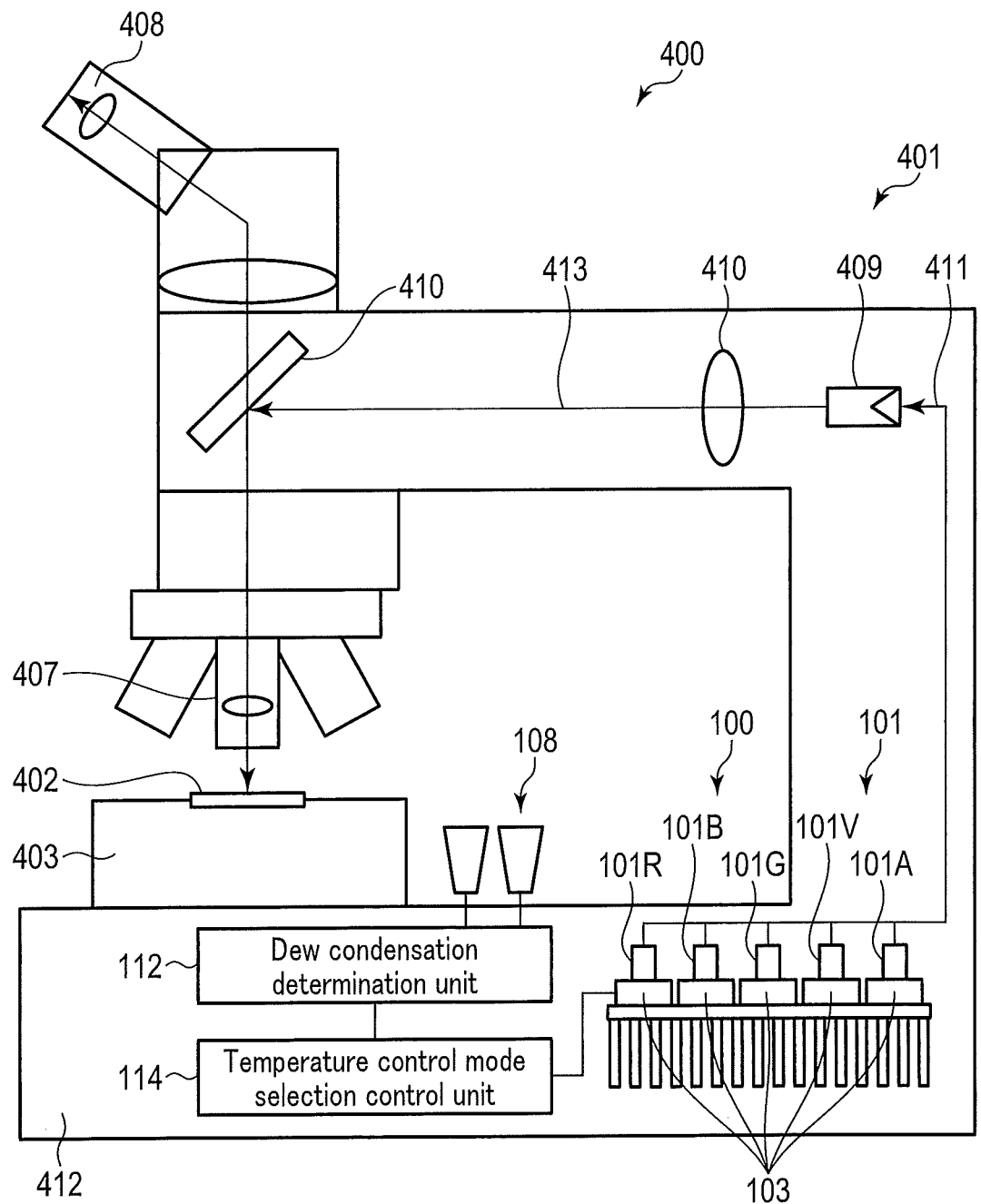
F I G. 19

ILLUMINATING DEVICE

CROSS-REFERENCE TO RELATED APPLICATIONS

This application is a Continuation Application of PCT Application No. PCT/JP2017/000668, filed Jan. 11, 2017, the entire contents of which are incorporated herein by reference.

BACKGROUND OF THE INVENTION

1. Field of the Invention

The present invention relates to an illuminating device including a semiconductor light source.

2. Description of the Related Art

For an illuminating device including a semiconductor light source, it is known that a temperature of the semiconductor light source is controlled in order to suppress or prevent occurrence of dew condensation. For example, Jpn. Pat. Appln. KOKAI Publication No. S61-79285 discloses the method of controlling the temperature of the semiconductor laser, in which when the dew-point temperature is low, the semiconductor laser is maintained at a predetermined temperature at which the set output can be obtained, whereas when the dew-point temperature is equal to or higher than the predetermined temperature, the semiconductor laser is set to have a temperature higher than the dew-point temperature.

BRIEF SUMMARY OF THE INVENTION

An illuminating device according to an embodiment of the present invention includes: a semiconductor light source; a temperature control unit that is disposed on the semiconductor light source and configured to control a temperature of the semiconductor light source to a desired temperature; a dew condensation determination unit configured to determine whether dew condensation may occur in the illuminating device based on at least one of a temperature associated with the illuminating device and an ambient environment condition of the illuminating device; and a temperature control mode selection control unit configured to select, as a temperature control mode of the temperature control unit, a dew condensation suppression mode in which the temperature control unit is caused to have a temperature that is higher than a predetermined temperature and equal to or less than an upper limit of a usable temperature of the semiconductor light source, based on priority items of operational control of the illuminating device and characteristics of the semiconductor light source, to temperature-control the temperature control unit, when the dew condensation determination unit determines that dew condensation may occur.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram schematically showing an example of the illuminating device according to the first embodiment;

FIG. 3 is a diagram schematically showing an example of a part of the illuminating device;

FIG. 4 is an enlarged view showing a circled portion denoted by C in FIG. 3;

FIG. 5 shows an example of priority item setting according to the first embodiment;

FIG. 7 shows an example of priority item setting according to a second embodiment;

FIG. 10 shows an example of priority item setting according to a third embodiment;

FIG. 11 shows an example of a control flow for suppressing dew condensation according to the third embodiment;

FIG. 13 is a block diagram schematically showing an example of an illuminating device according to a fourth embodiment;

FIG. 14 shows an example of priority item setting according to the fourth embodiment;

FIG. 16 shows an example of priority item setting according to a fifth embodiment;

FIG. 18 is a diagram schematically showing an endoscope system including an illuminating device according to a sixth embodiment; and FIG. 19 is a diagram schematically showing a microscope system including an illuminating device according to a seventh embodiment.

DETAILED DESCRIPTION OF THE INVENTION

First Embodiment

Figure 1:
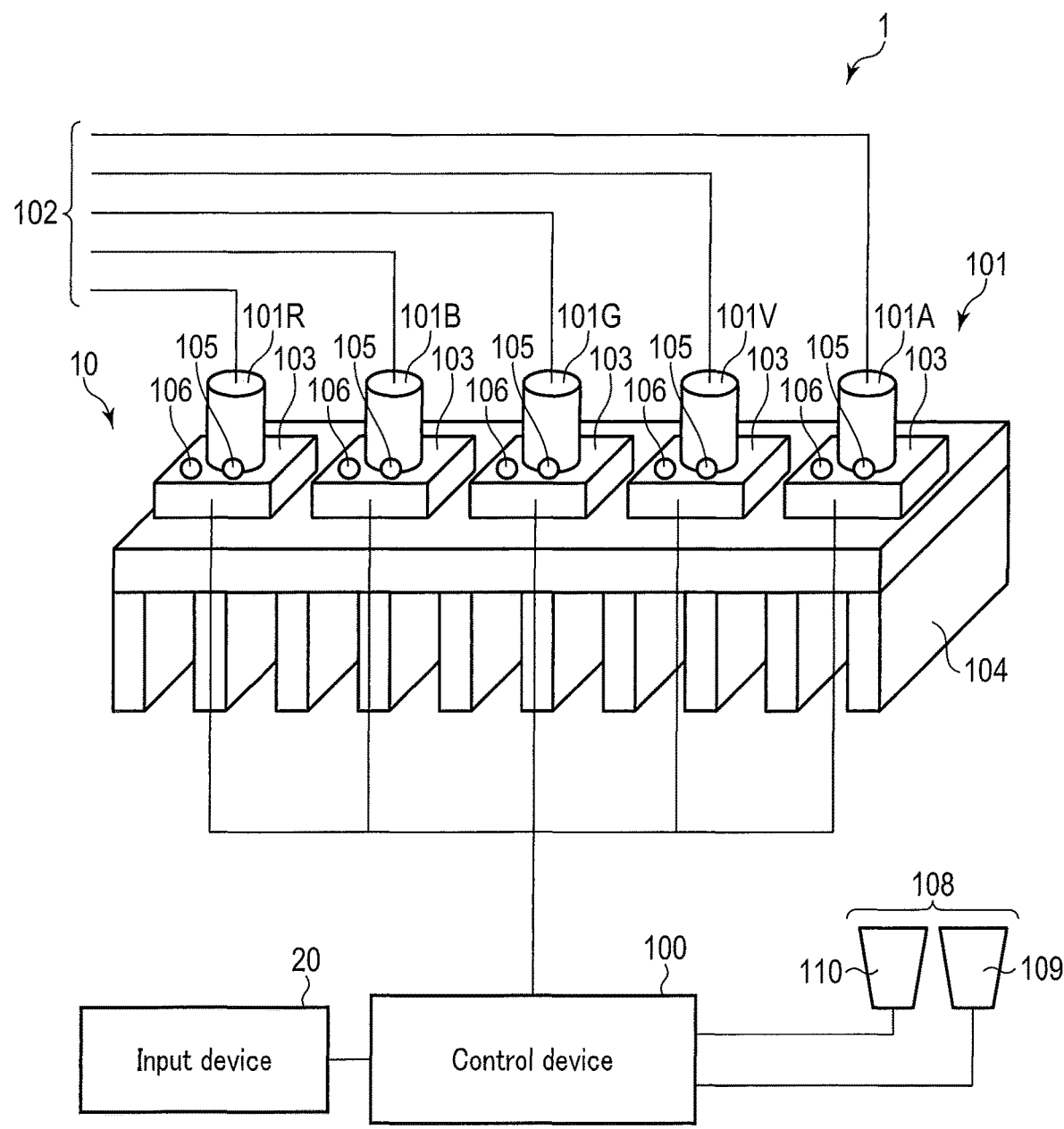
FIG. 1 is a diagram schematically showing an example of an illuminating device according to a first embodiment.

A first embodiment of the present invention will be described with reference to FIGS. 1 to 6. FIG. 1 is a diagram schematically showing an example of an illuminating device 1 according to the first embodiment. FIG. 2 is a block diagram schematically showing an example of the illuminating device 1. The illuminating device 1 includes a light source device 10, an input device 20, and a control device 100. The illuminating device 1 is used for illumination of a flexible tube insertion apparatus, which is, for example, an endoscope.

The light source device 10 includes one or more light sources 101. The light source 101 is a semiconductor light source configured to emit illumination light having desired optical characteristics, an example of which includes a laser diode (LD) light source, a light-emitting diode (LED) light source, and a super luminescent diode (SLD) light source. The light source 101 is electrically connected to a light source control unit 111 of the control device 100. The light source control unit 111 controls a drive current of a drive circuit (not shown) of the light source 101 to adjust a quantity of light emitted from the light source 101.

In the present embodiment, the light source device 10 includes light sources 101 of multiple colors in order to achieve optical characteristics appropriate for the illumination light of an endoscope. The light source 101 includes light sources of at least two colors selected from a red light source 101R, a blue light source 101B, a green light source 101G, a violet light source 101V, and an orange light source 101A. In the present embodiment, the light source 101 includes light sources of five colors of the red light source 101R, the blue light source 101B, the green light source 101G, the violet light source 101V, and the orange light source 101A. The light sources 101R, 101B, 101G, 101V, and 101A are connected to proximal ends of optical fibers 102, respectively. A distal end of each optical fiber 102 is optically connected to, for example, an endoscope (not shown).

Light emitted from the red light source 101R has a center wavelength λ of, for example, $640 \leq \lambda \leq 760$ nm. Light emitted from the green light source 101G has a center wavelength λ of, for example, $500 \leq \lambda \leq 590$ nm. Light emitted from the blue light source 101B has a center wavelength λ of, for example, $440 \leq \lambda \leq 500$ nm. Light emitted from the violet light source 101V has a center wavelength λ of, for example, $380 \leq \lambda \leq 440$ nm. Light emitted from the orange light source 101A has a center wavelength λ of, for example, $590 \leq \lambda \leq 610$ nm.

In general, a semiconductor light source has an upper limit of a usable temperature. In the present embodiment, the blue light source 101B and the green light source 101G have a usable temperature upper limit of 60° C. The red light source 101R, the violet light source 101V, and the orange light source 101A have a usable temperature upper limit of 40° C. The usable temperature upper limit is a limit of a driving temperature of the light source 101, which is determined in consideration of the specifications or the life of the light source 101. In general, it is known that if the driving temperature of the light source 101 rises from 25° C. to 60° C. through 90° C., a life (time until light-emitting efficiency drops to ½ of an initial value) is reduced to ¼ through ½. As the usable temperature upper limit, a rated use upper limit +10° C. may be used.

The red light source 101R, the blue light source 101B, and the green light source 101G have a wavelength shift limit temperature of 60° C. The violet light source 101V and the orange light source 101A have a wavelength shift limit temperature of 45° C. The wavelength shift limit temperature is a limit of the driving temperature of the light source 101 that is capable of maintaining optical characteristics in which an effect of special light observation described later can be expected.

FIG. 3 is a diagram schematically showing an example of a part of the illuminating device 1. The light sources 101 are disposed on temperature control units 103 that are heatable and coolable in order to control the temperature of the light sources 101, respectively. Therefore, each temperature control unit 103 can independently control the temperature of each of the light sources 101R, 101B, 101G, 101V, and 101A of the respective colors. Each temperature control unit 103 is, for example, a Peltier module (Peltier element). The temperature control units 103 may be disposed on a large heat sink 104 as shown in FIG. 1, or may each be disposed on a separate heat sink 104 as shown in FIG. 3. The heat sink 104 may be forcedly cooled by a fan (not shown) as necessary.

Each temperature control unit 103 is electrically connected to a temperature control mode selection control unit 114 of the control device 100. Each temperature control unit 103 is driven by each drive circuit (not shown) based on a control signal from the temperature control mode selection control unit 114.

As shown in FIG. 1, a light source temperature sensor 105 and a temperature control unit temperature sensor 106 are disposed on each temperature control unit 103. The light source temperature sensors 105 are sensors capable of measuring the temperature of the light sources 101R, 101B, 101G, 101V, and 101A, respectively. The temperature control unit temperature sensors 106 are sensors capable of measuring the temperature of the temperature control units 103, respectively. That is, the light source temperature sensor 105 and the temperature control unit temperature sensor 106 are sensors configured to measure the temperatures associated with the illuminating device.

FIG. 4 is an enlarged view showing a circled portion denoted by C in FIG. 3. FIG. 4 schematically shows an example of the structure of the portion where the light source 101 and the temperature control unit 103 are connected. A bracket 131 intervenes between the light source 101 and the temperature control unit 103, and the bracket 131 connects the light source 101 and the temperature control unit 103. A sensor groove 133 is provided on a light source mounting surface 132, which is a mounting surface on the light source 101 side of the bracket 131. The light source temperature sensor 105 is provided in the sensor groove 133 through a thermal interface material (TIM) 134. It is desirable for the bracket 131 to be a metal having a high thermal conductivity, such as copper or aluminum. The light source temperature sensor 105 is thermally connected to the light source mounting surface 132 through the TIM 134, and the temperature of the light source 101 can be measured by the light source temperature sensor 105. As the light source temperature sensor 105, a thermocouple, a thermistor, or the like can be considered. The light source temperature sensor 105 is preferably disposed in the vicinity of the light source mounting surface 132.

A sensor groove 136 is provided on a temperature control unit mounting surface 135 of the bracket 131 in the same manner as the light source mounting surface 132. In the sensor groove 136, the temperature control unit temperature sensor 106 is thermally connected to the temperature control unit mounting surface 135 through a TIM 134, and the temperature of the temperature control unit 103 can be measured by the temperature control unit temperature sensor 106. The temperature control unit temperature sensor 106 may be a thermocouple, a thermistor, or the like. The temperature control unit temperature sensor 106 is preferably disposed in the vicinity of a temperature control unit heat absorption surface 137 or the temperature control unit mounting surface 135.

An ambient environment condition collection sensor 108 configured to detect an ambient environment condition of the light source 101 or the temperature control unit 103 is disposed in the vicinity of the light source 101 or the temperature control unit 103. The ambient environment condition collection sensor 108 includes, for example, an ambient environment temperature sensor 109 and an ambient environment humidity sensor 110. The ambient environment condition collection sensor 108 may be a dew condensation sensor or the like.

The input device 20 is a general input device such as a keyboard. The input device 20 is electrically connected to the control device 100. Various commands for operating the control device 100 and apparatuses connected thereto are input to the input device 20. The input device 20 may be an operation panel provided in the control device 100 or a touch panel displayed on a display screen.

The control device 100 is configured by apparatuses including a CPU, etc. The control device 100 includes a light source control unit 111, a dew condensation determination unit 112, a storage unit 113, and a temperature control mode selection control unit 114.

The dew condensation determination unit 112 is connected to the light source temperature sensor 105, the temperature control unit temperature sensor 106, and the ambient environment condition collection sensor 108. The dew condensation determination unit 112 determines whether dew condensation occurs in at least one of the light source 101 and the temperature control unit 103, with reference to a detection value of ambient environment detected by the ambient environment condition collection sensor 108 (for example, outside air temperature detected by the ambient environment temperature sensor 109 and humidity detected by the ambient environment humidity sensor 110), and a detection value of at least one of the light source temperature sensor 105 and the temperature control unit temperature sensor 106. That is, the dew condensation determination unit 112 determines whether dew condensation may occur in the illuminating device 1 (the light source 101, the temperature control unit 103, or both) based on at least one of the temperature associated with the illuminating device 1 and the ambient environment condition of the illuminating device 1. The determination result by the dew condensation determination unit 112 is transmitted to the temperature control mode selection control unit 114.

In order to suppress the occurrence of dew condensation in the light source 101, it is preferable that the sensor referred to by the dew condensation determination unit 112 for determining the occurrence of dew condensation is the light source temperature sensor 105; however, if priority is given to dew condensation suppression of the temperature control unit 103 over the light source 101, the sensor may be the temperature control unit temperature sensor 106.

The storage unit 113 stores various types of information necessary for determining the occurrence of dew condensation in the dew condensation determination unit 112. The storage unit 113 further stores various target values (target temperatures) of a normal operation mode and a dew condensation suppression mode as temperature control modes selected by the temperature control mode selection control unit 114. In addition, the storage unit 113 stores information on priority item setting described later. The storage unit 113 may be an external recording medium.

The temperature control mode selection control unit 114 selects one of the normal operation mode and the dew condensation suppression mode as the temperature control mode of the temperature control unit 103, based on the determination result by the dew condensation determination unit 112. The normal operation mode is selected when the dew condensation determination unit 112 determines that no dew condensation may occur. The dew condensation suppression mode is selected when the dew condensation determination unit 112 determines that dew condensation may occur. The temperature control mode selection control unit 114 controls the drive current from the drive circuit (not shown) to the temperature control unit 103 based on the selected temperature control mode, thereby controlling the temperature of the light source 101 of each color and each temperature control unit 103.

In the normal operation mode, the target temperature of the light source 101 or the temperature control unit 103 is set to a first target value. The first target value is set, for example, to an approximately room temperature. In the dew condensation suppression mode, the target temperature of the light source 101 or the temperature control unit 103 is set to a second target value. The second target value is a predetermined temperature, which is, for example, 50° C. in the present embodiment. The second target value is higher than the first target value, and is desirably equal to or less than the upper limit of the usable temperature range of the light source 101. The second target value is set, for example, higher than the first target value by 5° C. or more. The upper limit of the usable temperature range may be an upper limit of the usable temperature range in the specification of the light source 101, or may be, for example, a driving temperature at which about half of the rating of the life of the light source 101 can be ensured.

The temperature control mode selection control unit 114 can determine the color of the light source 101 to which the dew condensation suppression mode is applied, and the application timing, based on the priority item setting.

FIG. 5 shows an example of priority item setting according to the first embodiment. The priority item setting includes, for example, at least one of light source life setting, special light observation setting, all-color dew condensation suppression setting, all-color dew condensation suppression disable setting, new light source setting, and special use setting. The light source life setting and the special light observation setting include light source setting and selection timing, respectively. In the light source setting, a color of light sources 101 to be targeted for priority items can be selected. That is, in the light source setting, a light source 101 targeted for temperature control is selected among the light sources 101 based on the optical characteristics of each of the light sources 101. The light source setting is, for example, setting relating to a color that each of the light sources 101 has. In the selection timing, a timing at which the temperature control mode is selected can be selected from "always", "outside air", "rewriting", "cumulative time", and "life exceeded".

The light source life setting is setting that gives priority to the life of the light source 101. If it is desired to give priority to a life over dew condensation suppression for a light source 101, this light source 101 is not selected in the light source life setting. The temperature control unit 103 disposed on the light source 101 of the color selected in the light source setting of the light source life setting can be driven in the dew condensation suppression mode. That is, the light source 101 of the selected color and the corresponding temperature control unit 103 can be temperature-controlled in the dew condensation suppression mode. In the present embodiment, the green light source 101G and the blue light source 101B are selected in the light source setting of the light source life setting. Further, "always" is selected for both the green light source 101G and the blue light source 101B for the selection timing of the light source life setting.

The special light observation setting is setting that gives priority to special light observation. If it is desired to give priority to special light observation over dew condensation suppression for a light source 101, this light source 101 is not selected in the special light observation setting. The temperature control unit 103 disposed on the light source 101 of the color selected in the light source setting of the special light observation setting can be driven in the dew condensation suppression mode. In the present embodiment, the red light source 101R, the green light source 101G, and the blue light source 101B are selected in the light source setting of the special light observation setting. Further, "always" is selected for the red light source 101R, the green light source 101G, and the blue light source 101B for the selection timing of the special light observation setting.

The special light observation is observation by an endoscope with illumination light using at least one of the violet light source 101V and the orange light source 101A. For example, for narrow band imaging (NBI), illumination light using the violet light source 101V and the green light source 101G is used for special light observation. Light emitted from the violet light source 101V has a center wavelength of λ=415 nm, while light emitted from the green light source 101G has a center wavelength of λ=540 nm. Since the light absorption characteristics of hemoglobin in blood have peaks in these wavelengths, use of light sources of these wavelengths allows the microscopic structure of biological mucous membrane to be observed with being emphasized as compared to an observation with normal white light. In addition, in endoscopic observation, special light observation aiming at accurate observation and diagnosis of a lesion area has been developed by adding orange color (A) to the three RGB colors producing ordinary white light to improve the color reproducibility and more accurately show the color tone of the biological mucous membrane.

In the priority item setting, it is possible to simultaneously select the light source life setting and the special light observation setting. As shown in FIG. 5, when both the light source life setting and the special light observation setting are selected, only the temperature control unit 103 disposed on the light source 101 of the color selected in both settings is driven in the dew condensation suppression mode. For example, since the red light source 101R is selected in the special light observation setting but not selected in the light source life setting, the temperature control unit 103 disposed on the red light source 101R is not targeted for operation in the dew condensation suppression mode. That is, the red light source 101R is not temperature-controlled in the dew condensation suppression mode. For example, since the green light source 101G and the blue light source 101B are selected in both the light source life setting and the special light observation setting, the temperature control units 103 disposed on the green light source 101G and the blue light source 101B are targeted for operation in the dew condensation suppression mode. While the light source life setting and the special light observation setting can be selected in duplicate, the light source 101 of a color not selected in any one of the settings does not shift to the dew condensation suppression mode (that is, is driven in the normal operation mode).

In the priority item setting, for the all-color dew condensation suppression setting, the all-color dew condensation suppression disable setting, the new light source setting, and the special use setting, it is possible to select colors of the light sources 101 to be targeted for priority items by the light source setting. For the priority item setting, when the light source life setting, the special light observation setting, or both of them are selected, it is not possible to select the all-color dew condensation suppression setting, the all-color dew condensation suppression disable setting, the new light source setting, or the special purpose setting.

For the light source setting of the all-color dew condensation suppression setting, all colors of the light sources 101R, 101G, 101B, 101V, and 101A are selected. For the light source setting of the all-color dew condensation suppression disable setting, none of the colors of the light sources 101R, 101G, 101B, 101V, and 101A is selected.

For the light source setting of the new light source setting, at least one light source 101 is selected. In FIG. 5, the red light source 101R is selected. The new light source setting is intended for use in selecting a color replaced when the light source 101 that has deteriorated due to the service or the like is replaced with a new light source 101.

For the light source setting of the special use setting, the violet light source 101V or the orange light source 101A is selected. In FIG. 5, the orange light source 101A is selected. The special use setting is intended for a light source 101 used only for very special use (i.e., expected to be rarely used).

The priority items can be set by the user inputting to the input device 20. Alternatively, the priority items are stored in advance in the storage unit 113. The priority items may be set by the user each time the illuminating device 1 is used, or those that have been already set may be read from the storage unit 113.

Figure 6:
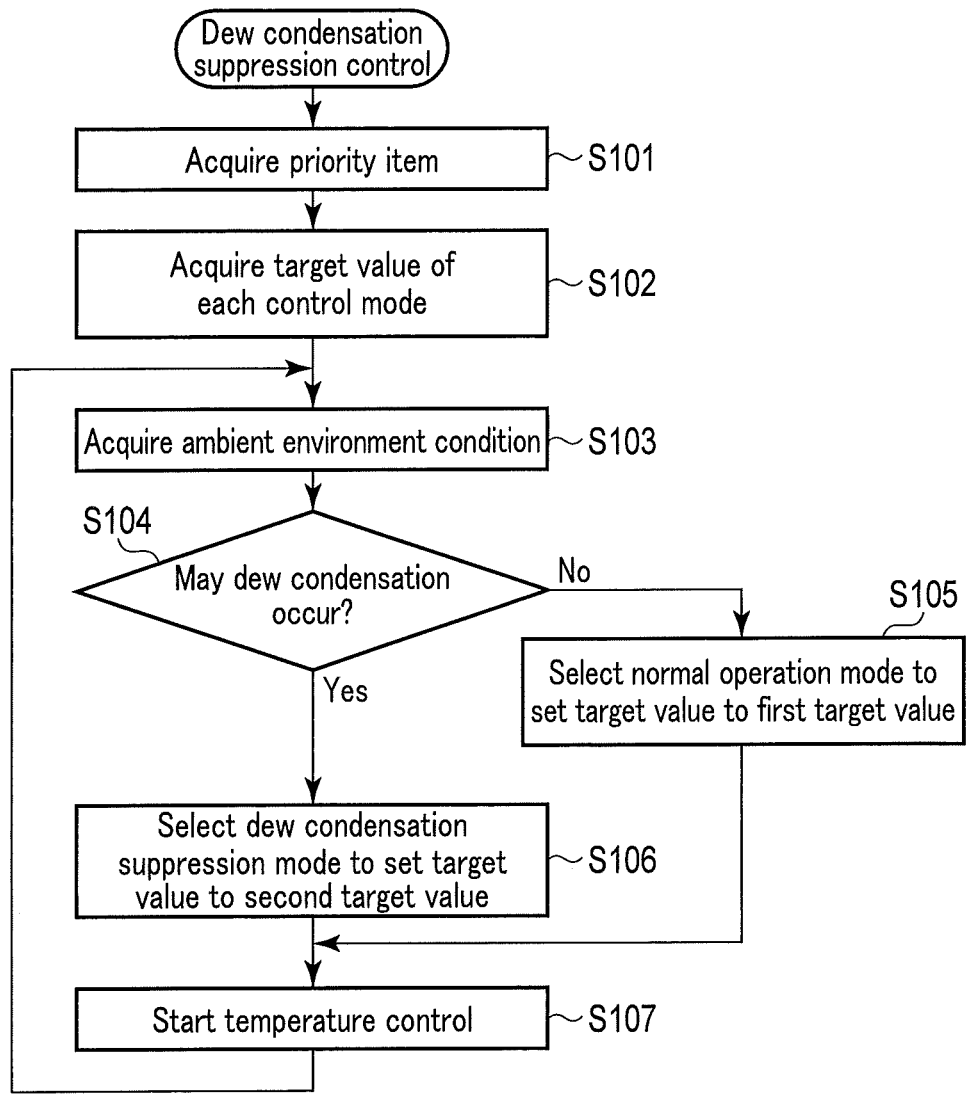
FIG. 6 shows an example of a control flow for suppressing dew condensation according to the first embodiment.

Next, a description will be given of an operation of the illuminating device 1 according to the present embodiment. FIG. 6 shows an example of a control flow for suppressing dew condensation of the illuminating device 1 according to the first embodiment.

In step S101, the temperature control mode selection control unit 114 of the control device 100 acquires information on the priority item setting input to the input device 20 through an input unit (not shown), or information on the priority item setting read from the storage unit 113. In step S102, the temperature control mode selection control unit 114 acquires a target temperature of each temperature control mode as in step S101. In step S103, the dew condensation determination unit 112 of the control device 100 acquires an ambient environment condition from the ambient environment condition collection sensor 108, and acquires a temperature of the light source 101 or the temperature control unit 103 from the light source temperature sensor 105 or the temperature control unit temperature sensor 106.

In step S104, the dew condensation determination unit 112 determines whether dew condensation may occur in the light source 101 or the temperature control unit 103, based on the ambient environment condition and the temperature acquired in step S103. For example, the dew condensation determination unit 112 determines whether dew condensation may occur in the light source 101 or the temperature control unit 103 by calculating a dew-point temperature from the temperature and the humidity acquired by the ambient environment temperature sensor 109 and the ambient environment humidity sensor 110, and then comparing the calculated dew-point temperature with the temperature of the light source 101 or the temperature control unit 103 acquired from the light source temperature sensor 105 or the temperature control unit temperature sensor 106.

If the dew condensation determination unit 112 determines in step S104 that no dew condensation may occur (No), the temperature control mode selection control unit 114 selects the normal operation mode as the temperature control mode to set the target temperatures of the light source 101 and the temperature control unit 103 to the first target temperature acquired in step S102 (step S105). That is, if the dew condensation determination unit 112 determines, with reference to the information from the ambient environment condition collection sensor 108, that no dew condensation may occur in the light source 101 or the temperature control unit 103, the temperature control mode selection control unit 114 selects the normal operation mode so that the temperatures of all the light sources 101 or the temperature control units 103 are controlled based on the normal operation mode regardless of the set contents in the priority item setting acquired in step S101. Then, the processing proceeds to step S107.

On the other hand, if the dew condensation determination unit 112 determines in step S104 that dew condensation may occur (Yes), the temperature control mode selection control unit 114 selects the dew condensation suppression mode as the temperature control mode to set the target temperatures of the light source 101 and the temperature control unit 103 to the second target temperature acquired in step S102 (step S106). That is, if the dew condensation determination unit 112 determines, with reference to the information from the ambient environment condition collection sensor 108, that a dew condensation may occur in the light source 101 or the temperature control unit 103, the temperature control mode selection control unit 114 selects the dew condensation suppression mode so that the temperatures of the light sources 101 or the temperature control units 103 are controlled based on the dew condensation suppression mode in accordance with the set contents in the priority item setting acquired in step S101. For example, when the temperature control unit 103 is already driven in the normal operation mode, the temperature control mode selection control unit 114 switches the temperature control mode from the normal operation mode to the dew condensation suppression mode in step S106. Then, the processing proceeds to step S107.

In the present embodiment, as shown in FIG. 5, the light source life setting and the special light observation setting are selected in the priority item setting, and for the light source setting of the light source life setting, the green light source 101G and the blue light source 101B are selected, while for the light source setting of the special light observation setting, the red light source 101R, the green light source 101G, and the blue light source 101B are selected. When both the light source life setting and the special light observation setting are selected as described above, since only the temperature control units 103 disposed on the light sources 101 of the colors selected in both settings are driven in the dew condensation suppression mode, the green light source 101G, the blue light source 101B, and their temperature control units 103 are targeted for temperature control in the dew condensation suppression mode.

If the all-color dew condensation suppression setting, not selected in FIG. 5, is selected in the priority item setting, the light sources 101 of all colors and their temperature control units 103 are targeted for temperature control in the dew condensation suppression mode. Similarly, if the all-color dew condensation suppression disable setting is selected, none of the light sources 101 and the temperature control units 103 is targeted for temperature control in the dew condensation suppression mode. If the new light source setting is selected, only the selected red light source 101R and its temperature control unit 103 are targeted for temperature control in the dew condensation suppression mode. If the special use setting is selected, only the selected orange light source 101A and its temperature control unit 103 are targeted for temperature control in the dew condensation suppression mode.

In step S107, the temperature control mode selection control unit 114 starts temperature control in the selected temperature control mode. Each temperature control unit 103 is driven by each drive circuit (not shown) based on a control signal from the temperature control mode selection control unit 114. After step S107, the processing returns to step S103, and the processing from step S103 is repeated.

For example, if the dew condensation determination unit 112 determines that dew condensation may occur, the temperature control mode selection control unit 114 causes the temperature control units 103 disposed on the light sources 101 selected in the priority item setting to be driven in the dew condensation suppression mode, controlling the temperatures so that the light sources 101 and the temperature control units 103 have the second target temperature of 50° C. Usually, since the ambient environment temperature assuming use of an endoscope is 45° C. or less, the light source 101 or the temperature control unit 103 whose temperature is controlled to 50° C. can suppress or prevent the occurrence of dew condensation.

For example, if the dew condensation determination unit 112 determines that no dew condensation may occur in a state where the temperature control mode selection control unit 114 selects the dew condensation suppression mode to perform temperature control, the temperature control mode selection control unit 114 switches the temperature control mode from the dew condensation suppression mode to the normal operation mode. Then, the temperature control mode selection control unit 114 controls the temperatures so that the light source 101 and the temperature control unit 103 have the first target temperature lower than the second target temperature. The light source 101 and the temperature control unit 103 are maintained at a relatively low temperature.

As described above, according to the present embodiment, in the control device 100, when the dew condensation determination unit 112 determines that dew condensation may occur, the temperature control mode selection control unit 114 controls the temperature of the selected light source 101 and its temperature control unit 103 in the dew condensation suppression mode, based on the operational control priority items of the illuminating device and the characteristics of each of the light sources 101. The dew condensation suppression mode is a temperature control mode in which the temperature control unit 103 is caused to have a temperature higher than a predetermined temperature (for example, the first target value in the normal operation mode) and equal to or less than the upper limit of the usable temperature of the light source 101. Thereby, the light source 101 and the temperature control unit 103 are each maintained at a temperature higher than the ambient environment temperature by relatively simple control. Therefore, it is possible to suppress or prevent the occurrence of dew condensation in the light source 101 and the temperature control unit 103 in accordance with the characteristics and the operational conditions of the illuminating device 1.

In the present embodiment, the target temperature of the light source 101 and the temperature control unit 103 in the dew condensation suppression mode is set in consideration of the usable upper limit temperature and the wavelength shift limit temperature. For this reason, even if the temperature control unit 103 is driven in the dew condensation suppression mode, it is possible to prevent the reduction in the life, the reduction in the light-emitting efficiency, the shift of the center wavelength of the emitted light, etc., which may occur when the temperature of the light source 101 becomes high.

In the present embodiment, the temperature control mode selection control unit 114 selects the light source 101 and the temperature control unit 103 whose temperature is controlled in the dew condensation suppression mode based on the priority item setting and the characteristics of the light sources 101. Accordingly, if it is desired to give priority to functions such as a life or an optical performance in special light observation of a specific light source 101, this light source 101 is removed from the selection in the priority item setting. This allows giving priority to functions for prioritization other than the dew condensation suppression function in certain light sources 101, while giving priority to the dew condensation suppression function in the other light sources 101. Therefore, the illuminating device 1 can provide dew condensation suppression functions in accordance with various characteristics and operational conditions of the illuminating device 1.

Second Embodiment

Figure 8:
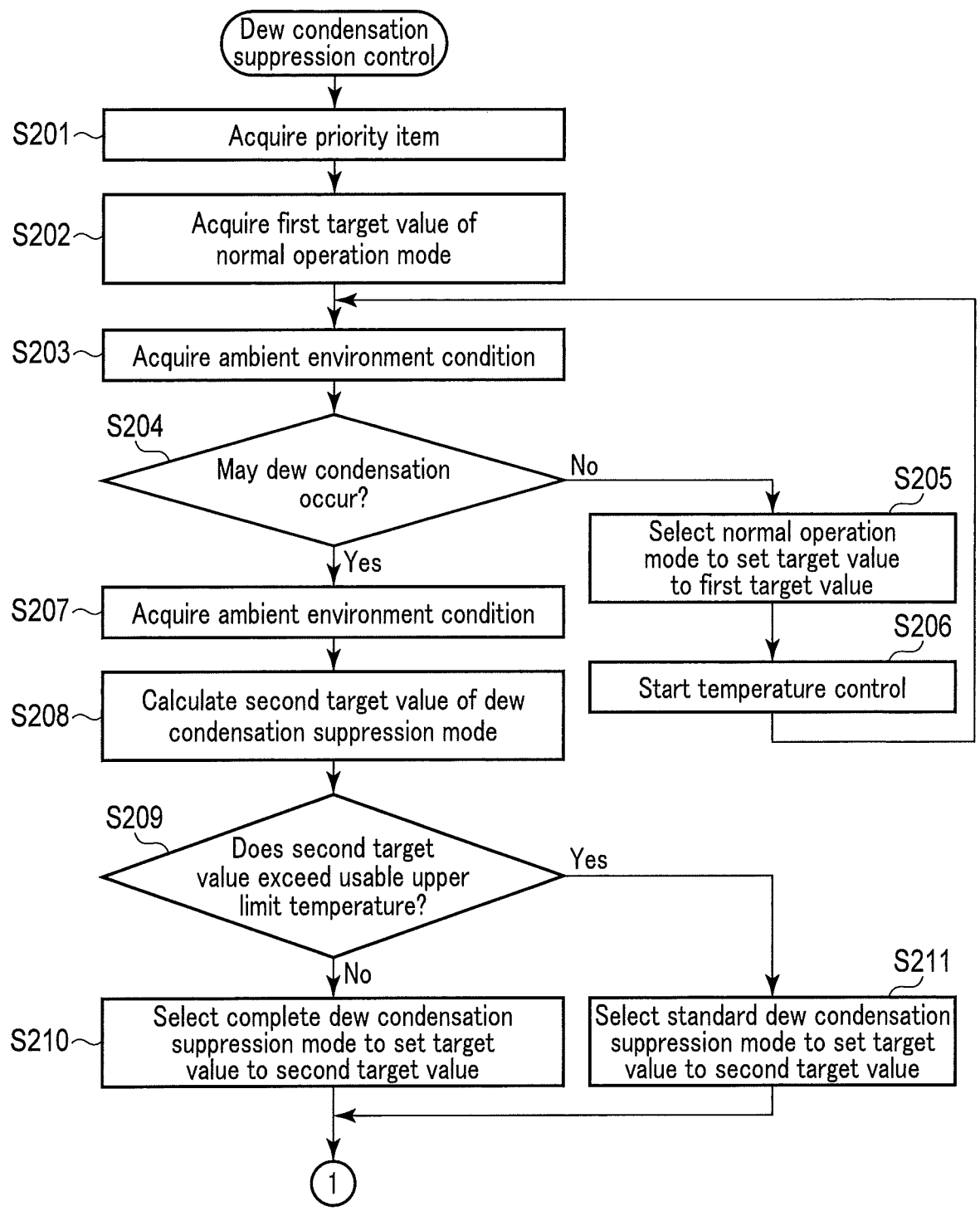
FIG. 8 shows an example of a control flow for suppressing dew condensation according to the second embodiment.
Figure 9:
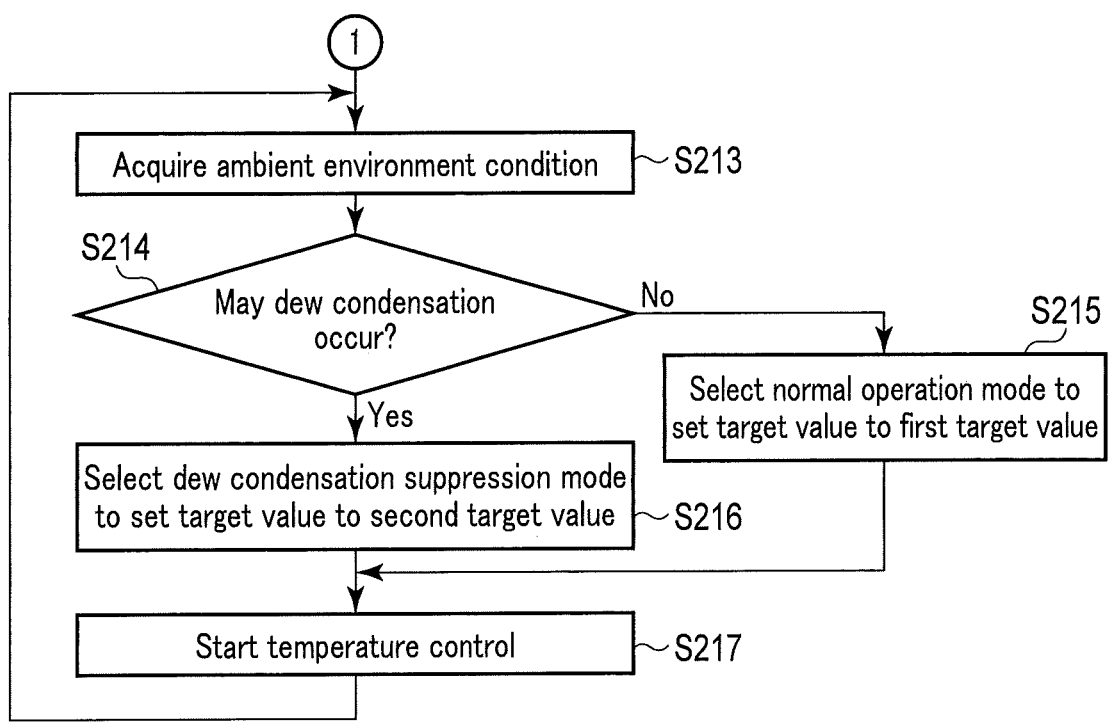
FIG. 9 shows an example of a control flow for suppressing dew condensation according to the second embodiment.

A second embodiment of the present invention will be described with reference to FIGS. 7 to 9. The following description mainly describes differences from the first embodiment. In the second embodiment, the selection timing of the light source life setting and the special light observation setting in the priority item setting differs from that in the first embodiment. That is, in the first embodiment, "always" is selected for the timing for selecting the temperature control mode, but in the second embodiment, "outside air" is selected.

FIG. 7 shows an example of priority item setting according to the second embodiment. For the selection timing of the light source life setting in the priority item setting, "outside air" is selected for both the green light source 101G and the blue light source 101B. Further, for the selection timing of the special light observation setting, "outside air" is selected for the red light source 101R, the green light source 101G, and the blue light source 101B.

Next, a description will be given of an operation of the illuminating device 1 according to the present embodiment. FIGS. 8 and 9 show an example of a control flow for suppressing dew condensation of the illuminating device 1 according to the present embodiment.

In step S201, the temperature control mode selection control unit 114 acquires information on priority item setting in the same manner as step S101 in the first embodiment. In step S202, the temperature control mode selection control unit 114 acquires the first target temperature of the normal operation mode in the same manner as step S102. In step S203, the dew condensation determination unit 112 of the control device 100 acquires the ambient environment condition from the ambient environment condition collection sensor 108, and acquires the temperature of the light source 101 or temperature control unit 103 from the light source temperature sensor 105 or the temperature control unit temperature sensor 106.

In step S204, the dew condensation determination unit 112 determines whether dew condensation may occur in the light source 101 or the temperature control unit 103 in the same manner as step S103, based on the ambient environment condition and the temperature acquired in step S203.

If the dew condensation determination unit 112 determines in step S204 that no dew condensation may occur (No), the temperature control mode selection control unit 114 selects the normal operation mode as the temperature control mode to set the target values of the light source 101 and the temperature control unit 103 to the first target temperature acquired in step S202 (step S205). Then, in step S206, the temperature control mode selection control unit 114 starts temperature control in the normal operation mode. After step S206, the processing returns to step S203, and the processing from step S203 is repeated.

On the other hand, if the dew condensation determination unit 112 determines in step S204 that dew condensation may occur (Yes), the dew condensation determination unit 112 acquires the ambient environment temperature from the ambient environment temperature sensor 109 (step S207). Then, in step S208, the temperature control mode selection control unit 114 calculates the second target temperature of the dew condensation suppression mode based on the ambient environment temperature acquired by the dew condensation determination unit 112 in step S207.

The second target temperature is obtained by adding a predetermined correction value to the output value of the ambient environment temperature sensor 109 acquired in step S207. The correction value is a value having a temperature unit (° C.) for calculating the second target temperature by the addition to the output value of the ambient environment temperature sensor 109, and is a value unique to each light source 101. While the correction value is desirably a value of 5° C. or more for providing an appropriate condensation suppression effect, the second target temperature is desirably a value 5° C. or more higher than the temperature output from the ambient environment temperature sensor 109 and not exceeding the usable upper limit temperature of the light source 101.

In step S209, the temperature control mode selection control unit 114 determines whether the second target temperature calculated in step S208 exceeds the usable upper limit temperature of the light source 101, and whether the second target temperature exceeds the wavelength shift limit temperature of the light source 101. The determination as to whether the second target temperature exceeds the usable upper limit temperature of the light source 101 is performed when the light source life setting is selected in the priority item setting acquired in step S201. The determination as to whether the second target temperature exceeds the wavelength shift limit temperature of the light source 101 is performed when the special light observation setting is selected in the priority item setting acquired in step S201.

If the temperature control mode selection control unit 114 determines in step S209 that the second target temperature neither exceeds the usable upper limit temperature of the light source 101 nor the wavelength shift limit temperature (No), the temperature control mode selection control unit 114 selects the dew condensation suppression mode as the temperature control mode to set the target temperatures of the light sources 101 and the temperature control units 103 to the second target temperature calculated in step S208 for the light sources 101 of all colors regardless of contents of the light source setting in the priority item setting acquired in step S201 (step S210). That is, the temperature control units 103 disposed on the light sources 101 of colors not selected in the light source setting in the priority item setting are also targeted for temperature control in the dew condensation suppression mode. The dew condensation suppression mode selected in step S210 will be referred to as a complete dew condensation suppression mode.

If the light source life setting is selected in the priority item setting, for example, when the output value of the ambient environment temperature sensor 109 is 30° C. and the correction value is 5° C., thus, the second target value is 35° C., since the usable upper limit temperature of the light source 101 is 40° C. or higher for all colors, the usable upper limit temperature is higher than 35° C. of the second target value. Therefore, regardless of the selection in the light source setting, the temperature control unit 103 is temperature-controlled in the complete dew condensation suppression mode.

If the special light observation setting is selected in the priority item setting, for example, when the output value of the ambient environment temperature sensor 109 is 40° C. and the correction value is 5° C., thus, the second target value is 45° C., since the wavelength shift limit temperature of the light source 101 is 45° C. or higher for all colors, the wavelength shift limit temperature is equal to or higher than 45° C. of the second target value. Therefore, regardless of the selection in the light source setting, the temperature control unit 103 is temperature-controlled in the complete dew condensation suppression mode.

On the other hand, if the temperature control mode selection control unit 114 determines in step S209 that the second target value exceeds the usable upper limit temperature of the light source 101 or exceeds the wavelength shift limit temperature (Yes), the temperature control mode selection control unit 114 selects the dew condensation suppression mode as the temperature control mode to set the target temperatures of the light source 101 and its temperature control unit 103 to the second target temperature calculated in step S208 in accordance with the contents of the light source setting in the priority item setting acquired in step S201 (step S211). That is, the temperature control units 103 whose temperatures are controlled in the dew condensation suppression mode are only the temperature control units 103 disposed on the light sources 101 of the colors selected in the light source setting. The temperature control units 103 disposed on the light sources 101 of the colors not selected in the light source setting are temperature-controlled in the normal operation mode. The dew condensation suppression mode selected in step S211 will be referred to as a standard dew condensation suppression mode.

If the light source life setting is selected in the priority item setting, for example, when the output value of the ambient environment temperature sensor 109 is 40° C. and the correction value is 5° C., thus, the second target value is 45° C., since the usable upper limit temperature of the blue light source 101B and the green light source 101G is 60° C., the usable upper limit temperature is higher than the second target value. On the other hand, since the usable upper limit temperature of the red light source 101R, the violet light source 101V, and the orange light source 101A is 40° C., the usable upper limit temperature is lower than the second target value. Therefore, the temperature control unit 103 is temperature-controlled in the standard dew condensation suppression mode.

If the special light observation setting is selected in the priority item setting, for example, when the output value of the ambient environment temperature sensor 109 is 45° C. and the correction value is 5° C., thus, the second target value is 50° C., since the wavelength shift limit temperature of the blue light source 101B and the green light source 101G is 60° C., the wavelength shift limit temperature is higher than the second target value. On the other hand, the wavelength shift limit temperature of each of the red light source 101R, the violet light source 101V, and the orange light source 101A is 45° C., the wavelength shift limit temperature is lower than the second target value. Therefore, the temperature control unit 103 is temperature-controlled in the standard dew condensation suppression mode.

After step S210 or S211, the processing proceeds to step S212. In step S212, the temperature control mode selection control unit 114 starts temperature control in the selected temperature control mode.

In step S213, the dew condensation determination unit 112 acquires the ambient environment condition and the temperature of the light source 101 or the temperature control unit 103 as in step S203. Then, in step S214, the dew condensation determination unit 112 determines whether dew condensation may occur in the light source 101 or the temperature control unit 103 in the same manner as in step S204, based on the ambient environment condition and the temperature acquired in step S213.

If the dew condensation determination unit 112 determines in step S214 that no dew condensation may occur (No), the temperature control mode selection control unit 114 selects the normal operation mode as the temperature control mode to set the target temperatures of the light source 101 and the temperature control unit 103 to the first target temperature acquired in step S202 (step S215). On the other hand, if the dew condensation determination unit 112 determines that dew condensation may occur (Yes), the temperature control mode selection control unit 114 selects the dew condensation suppression mode as the temperature control mode to set the target temperatures of the light source 101 and the temperature control unit 103 to the second target temperature calculated in step S208 (step S216). The dew condensation suppression mode selected here is the complete dew condensation suppression mode according to step S210, or the standard condensation suppression mode according to step S211.

After step S215 or S216, the processing proceeds to step S217. In step S217, the temperature control mode selection control unit 114 starts temperature control in the selected temperature control mode. After step S217, the processing returns to step S213, and the processing from step S213 is repeated.

According to the present embodiment, the second target temperature may be set to a lower temperature than in the first embodiment. The low driving temperature of the light source 101 allows prolonging the life of the light source 101 or improving the light-emitting efficiency. Therefore, in the present embodiment, it is possible to provide an illuminating device having a longer life and higher light-emitting efficiency than that of the first embodiment.

For example, by setting the correction value to +5° C., it is possible to suppress or prevent the occurrence of dew condensation while minimizing the load increase on the light source 101. In addition, if the correction value is set to +10° C., there is a certain degree of increase in load on the light source 101, but this is not a level at which the light source 101 immediately becomes broken. Thus, it is possible to complete the work in progress while suppressing or preventing the occurrence of dew condensation of the light source 101 or the temperature control unit 103.

Moreover, since the temperature of the light source 101 can be controlled to be higher than the ambient environment temperature, the occurrence of dew condensation can be reduced.

Furthermore, lowering the driving temperature of the light source 101 reduces the center wavelength shift of the light emitted from the light source 101, so that the color change is reduced. It is therefore possible to obtain more reliable effects of special light observation.

Third Embodiment

A third embodiment of the present invention will be described with reference to FIGS. 10 to 12. The following description mainly describes differences from the second embodiment. In the third embodiment, the selection timing for the light source life setting and the special light observation setting in the priority item setting differs from that in the second embodiment. That is, in the second embodiment, "outside air" is selected as the timing for selecting the temperature control mode, but in the third embodiment, "rewriting" is selected.

FIG. 10 shows an example of priority item setting according to the third embodiment. For the selection timing of the light source life setting in the priority item setting, "rewriting" is selected for both the green light source 101G and the blue light source 101B. Further, for the selection timing of the special light observation setting, "rewriting" is selected for the red light source 101R, the green light source 101G, and the blue light source 101B.

When "rewriting" is selected, after the second target temperature is determined in the same manner as in the second embodiment, the ambient environment condition collection sensor 108 detects the ambient environment temperature by real-time measurements that continue with a desired sampling period, and the temperature control mode selection control unit 114 rewrites the second target temperature with a desired period based on the detected ambient environment temperature to cause the storage unit 113 to store it. That is, during the period when the dew condensation determination unit 112 determines that dew condensation may occur, the measurement of the ambient environment temperature, the setting of the second target temperature, the selection of the temperature control mode based on the priority items, and the determination of presence or absence of the dew condensation occurrence are repeated in this order.

Next, a description will be given of an operation of the illuminating device 1 according to the present embodiment. FIG. 11 shows an example of a control flow for suppressing dew condensation of the illuminating device 1 according to the present embodiment.

Steps S301 to S304 are the same as steps S201 to S204 in the second embodiment, respectively. In step S304, the dew condensation determination unit 112 determines whether dew condensation may occur in the light source 101 or the temperature control unit 103, based on the ambient environment condition and temperature acquired in step S303.

If the dew condensation determination unit 112 determines in step S304 that no dew condensation may occur (No), the temperature control mode selection control unit 114 selects the normal operation mode as the temperature control mode to set the target values of the light source 101 and the temperature control unit 103 to the first target temperature (step S305). Then, the processing proceeds to step S311.

On the other hand, if the dew condensation determination unit 112 determines in step S304 that dew condensation may occur (Yes), the dew condensation determination unit 112 acquires the ambient environment temperature from the ambient environment temperature sensor 109 (step S306). Then, in step S307, the temperature control mode selection control unit 114 calculates the second target temperature of the dew condensation suppression mode based on the ambient environment temperature acquired by the dew condensation determination unit 112 in step S306. The second target temperature is set in the same manner as in the second embodiment. Then, the processing proceeds to step S308.

Steps S308 to S310 are the same as steps S209 to S211 of the second embodiment, respectively. That is, the temperature control mode selection control unit 114 determines whether the second target temperature calculated in step S307 exceeds the usable upper limit temperature of the light source 101, and whether the second target temperature exceeds the wavelength shift limit temperature of the light source 101, and then, based on this determination, selects the complete dew condensation suppression mode or the standard dew condensation suppression mode as the temperature control mode.

After step S305, S309, or S310, the processing proceeds to step S311. In step S311, the temperature control mode selection control unit 114 starts temperature control in the selected temperature control mode. After step S311, the processing returns to step S303, and the processing from step S303 is repeated.

Figure 12:
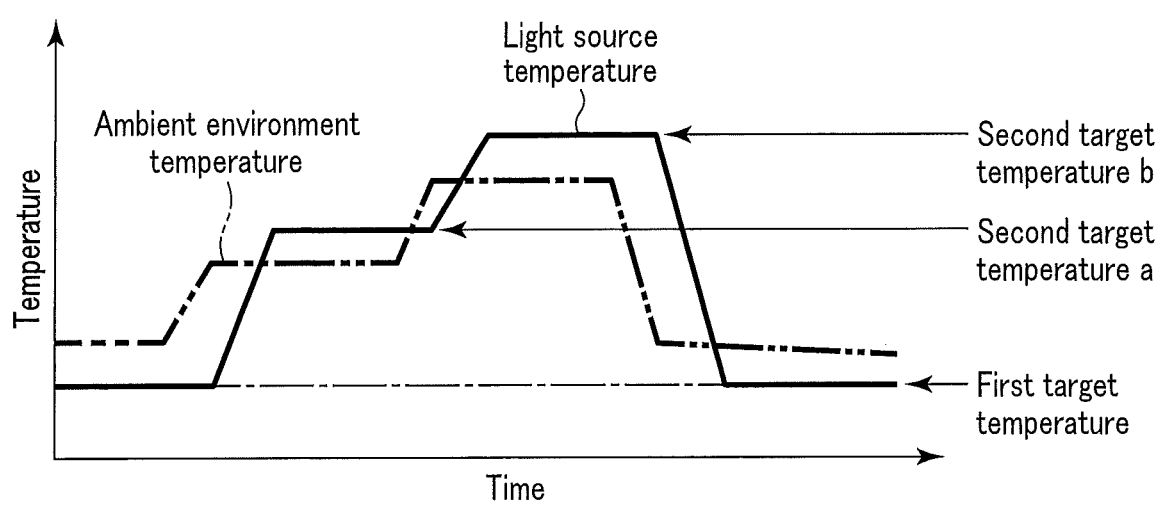
FIG. 12 shows an example of temporal changes in an ambient environment temperature, a light source temperature, a first target temperature, and a second target temperature according to the third embodiment.

FIG. 12 shows an example of temporal changes in an ambient environment temperature, a light source temperature, a first target temperature, and a second target temperature according to the third embodiment. In the present embodiment, the temperature control mode selection control unit 114 rewrites the second target temperature with a desired period as described above. That is, the second target value is given as a function of temperature. As an example, FIG. 12 shows a second target temperature a, and a second target temperature b that is higher than the second target temperature a.

In the third embodiment, even if the ambient environment temperature changes after the second target temperature is set, it is possible to perform temperature control with a more appropriate second target value as compared to the second embodiment. For example, if a change in ambient conditions such as increase in the ambient environment temperature occurs, the second target value can be set higher in accordance with the increase in temperature. In addition, if the ambient environment temperature drops after the second target value is set first, the second target value can be set lower in accordance with the decrease in temperature. Therefore, in the third embodiment, as compared to the second embodiment, it is possible to perform dew condensation suppression control adapted to changes in the ambient environment temperature, and to suppress dew condensation in a more reliable manner. In addition, it is possible to provide an illuminating device expected to prolong the life of the light source 101 and to improve the optical characteristics (light-emitting efficiency and special light observation effect).

Fourth Embodiment

Figure 15:
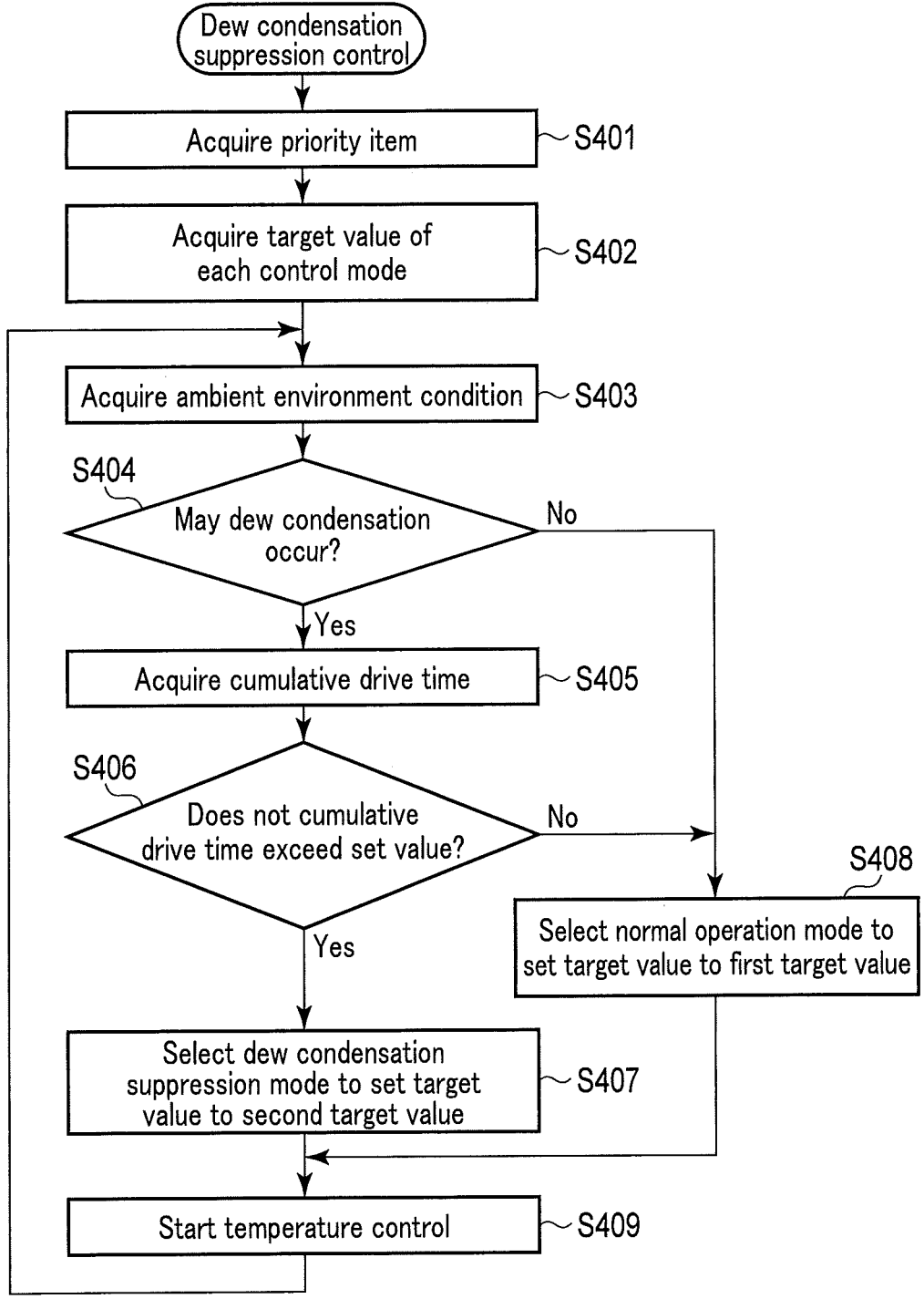
FIG. 15 shows an example of a control flow for suppressing dew condensation according to the fourth embodiment.

A fourth embodiment of the present invention will be described with reference to FIG. 13 to FIG. 15. The following description mainly describes differences from the first embodiment.

FIG. 13 is a block diagram schematically showing an example of an illuminating device according to the fourth embodiment. In the present embodiment, the light source device 10 includes drive time measurement units 107. The drive time measurement units 107 are provided in the light sources 101, respectively. The drive time measurement units 107 measure the drive time of the light sources 101, respectively. The drive time measurement unit 107 includes a storage unit (not shown) configured to store cumulative drive time of the light source 101. Alternatively, the cumulative drive time of each light source 101 may be stored in the storage unit 113 of the control device 100. The storage unit 113 stores a threshold (set value) of the cumulative drive time of each light source 101. The threshold of the cumulative drive time is assumed to be, for example, approximately ¾ of the life of each light source 101. This intends the light source 101 with little remaining life to be refrained from driving in the dew condensation suppression mode. The set value can be set by the user inputting from the input device 20.

FIG. 14 shows an example of priority item setting according to the fourth embodiment. For the selection timing of the light source life setting in the priority item setting, "cumulative time" is selected in addition to "always" for both the green light source 101G and the blue light source 101B. The "cumulative time" is an option selected along with "always", "outside air", or "rewriting".

Next, a description will be given of an operation of the illuminating device 1 according to the present embodiment. FIG. 15 shows an example of a control flow for suppressing dew condensation of the illuminating device 1 according to the fourth embodiment. This corresponds to the control flow for suppressing dew condensation of the illuminating device 1 according to the first embodiment, but includes determining if the cumulative drive time does not exceed the set value.

Steps S401 to S404 are the same as steps S101 to S104 of the first embodiment, respectively. In step S404, the dew condensation determination unit 112 determines whether dew condensation may occur in the light source 101 or the temperature control unit 103, based on the ambient environment condition and temperature acquired in step S403.

If the dew condensation determination unit 112 determines in step S404 that no dew condensation may occur (No), the temperature control mode selection control unit 114 selects the normal operation mode as the temperature control mode to set the target temperatures of the light source 101 and the temperature control unit 103 to the first target temperature (step S408). Then, the processing proceeds to step S409.

On the other hand, if the dew condensation determination unit 112 determines in step S404 that dew condensation may occur (Yes), the temperature control mode selection control unit 114 acquires the cumulative drive time of the light source 101 from the drive time measurement unit 107 (step S405). Then, in step S406, the temperature control mode selection control unit 114 determines whether the cumulative drive time does not exceed the set value of the cumulative drive time stored in the storage unit 113 (step S406).

If the temperature control mode selection control unit 114 determines in step S406 that the cumulative drive time does not exceed the set value (Yes), the temperature control mode selection control unit 114 selects the dew condensation suppression mode as the temperature control mode to set the target temperatures of the light source 101 and the temperature control unit 103 to the second target temperature acquired in step S402 (step S407). Then, the processing proceeds to step S409.

On the other hand, if the temperature control mode selection control unit 114 determines in step S406 that the cumulative drive time exceeds the set value (No), the temperature control mode selection control unit 114 selects the normal operation mode as the temperature control mode to set the target temperatures of the light source 101 and the temperature control unit 103 to the first target temperature acquired in step S402 (step S408). Then, the processing proceeds to step S409.

In step S409, the temperature control mode selection control unit 114 starts temperature control in the selected temperature control mode. After step S409, the processing returns to step S403, and the processing from step S403 is repeated.

According to the present embodiment, it is possible to set the timing for selecting the dew condensation suppression mode in a more precise manner as compared to the first to third embodiments. Therefore, it is possible to provide an illuminating device in which improvement in the life of the light source 101 can be expected as compared to those according to the first to third embodiments.

In the above description, as the fourth embodiment, the determination of whether the cumulative drive time does not exceed the set value is added to the control flow for suppressing dew condensation in the illuminating device 1 according to the first embodiment. However, the determination of whether the cumulative drive time does not exceed the set value may be added to the control flow for suppressing dew condensation in the illuminating device 1 according to the second or third embodiment. That is, even when "cumulative time" is selected in addition to "outside air" or "rewriting" for the selection timing of the light source life setting in the priority item setting, the similar advantageous effect can be obtained, and it is therefore included in the fourth embodiment.

Fifth Embodiment

Figure 17:
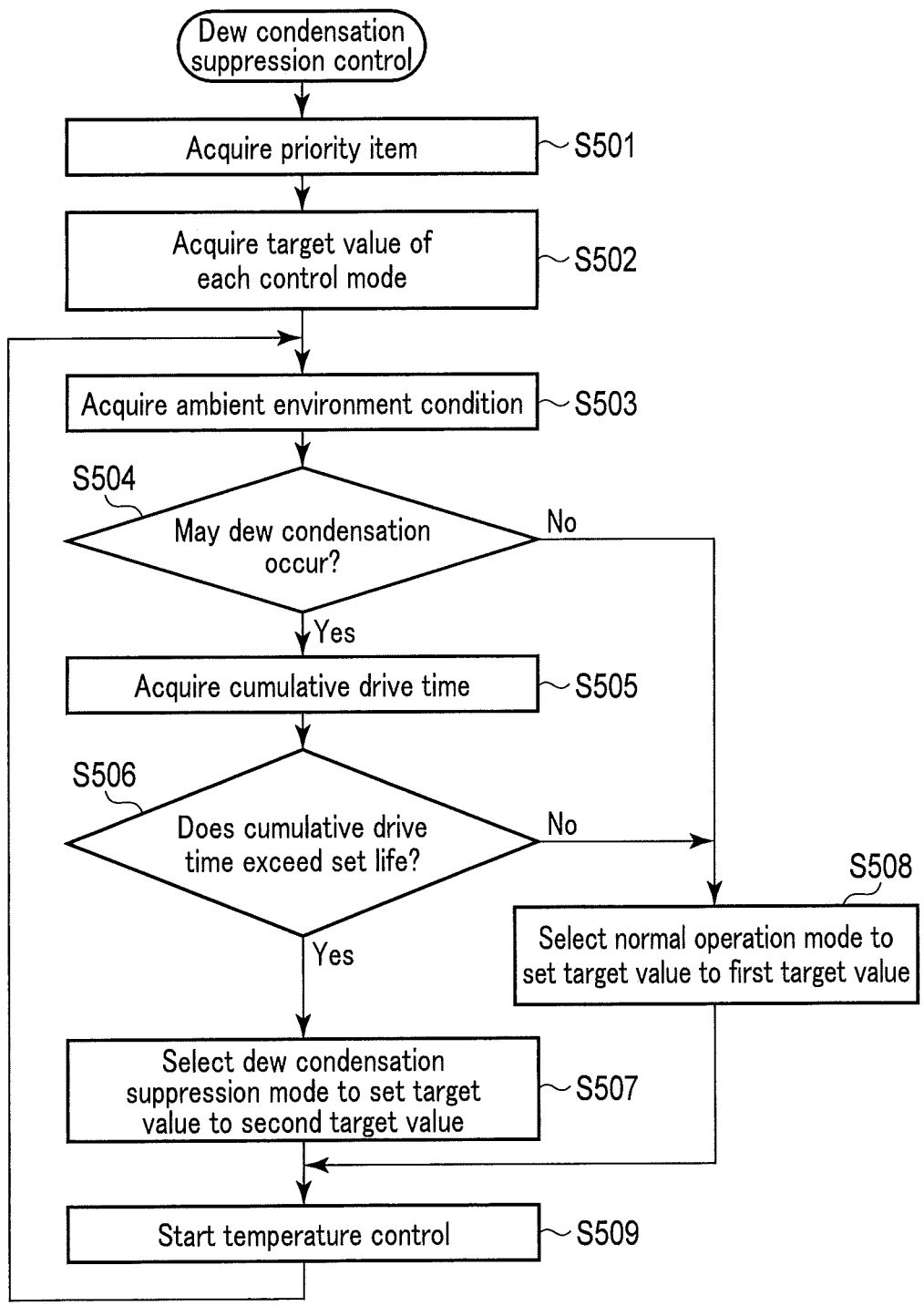
FIG. 17 shows an example of a control flow for suppressing dew condensation according to the fifth embodiment.

A fifth embodiment of the present invention will be described with reference to FIGS. 16 and 17. The following description mainly describes differences from the fourth embodiment.

FIG. 16 shows an example of priority item setting according to the fifth embodiment. For the selection timing of the light source life setting in the priority item setting, "life exceeded" is selected in addition to "always" for both the green light source 101G and the blue light source 101B. The "life exceeded" is an option selected along with "always", "outside air", or "rewriting".

Next, a description will be given of an operation of the illuminating device 1 according to the present embodiment. FIG. 17 shows an example of a control flow for suppressing dew condensation of the illuminating device 1 according to the fifth embodiment. This corresponds to the control flow for suppressing dew condensation of the illuminating device 1 according to the first embodiment, but includes determination of whether the cumulative drive time exceeds the set life.

Steps S501 to S505 are the same as steps S401 to S405 of the fourth embodiment, respectively. In step S504, the dew condensation determination unit 112 determines whether dew condensation may occur in the light source 101 or the temperature control unit 103, based on the ambient environment condition and temperature acquired in step S503.

If the dew condensation determination unit 112 determines in step S504 that no dew condensation may occur (No), the temperature control mode selection control unit 114 selects the normal operation mode as the temperature control mode to set the target temperatures of the light source 101 and the temperature control unit 103 to the first target temperature (step S508). Then, the processing proceeds to step S509.

On the other hand, if the dew condensation determination unit 112 determines in step S504 that dew condensation may occur (Yes), the temperature control mode selection control unit 114 acquires the cumulative drive time of the light source 101 from the drive time measurement unit 107 (step S505). Then, in step S506, the temperature control mode selection control unit 114 determines whether the cumulative drive time exceeds the set life of the cumulative drive time stored in the storage unit 113 (step S506).

If the temperature control mode selection control unit 114 determines in step S506 that the cumulative drive time exceeds the set life (Yes), the temperature control mode selection control unit 114 selects the dew condensation suppression mode as the temperature control mode to set the target temperatures of the light source 101 and the temperature control unit 103 to the second target temperature acquired in step S502 (step S507). Then, the processing proceeds to step S509.

On the other hand, if the temperature control mode selection control unit 114 determines in step S506 that the cumulative drive time does not exceed the set life (No), the temperature control mode selection control unit 114 selects the normal operation mode as the temperature control mode to set the target temperature of the temperature control unit 103 to the first target temperature acquired in step S402 (step S508). Then, the processing proceeds to step S509.

In step S509, the temperature control mode selection control unit 114 starts temperature control in the selected temperature control mode. After step S509, the processing returns to step S503, and the processing from step S503 is repeated.

In the present embodiment, the temperature control mode selection control unit 114 selects the dew condensation suppression mode only when the cumulative drive time of the selected light source 101 exceeds the set life of the light source 101. The present embodiment assumes the case where the light source 101 having exceeded the life may be actively driven in the dew condensation suppression mode.

According to the present embodiment, the temperature control mode selection control unit 114 actively drives the light source 101 having exceeded the life in the dew condensation suppression mode. Although driving in the dew condensation suppression mode at a relatively high temperature reduces the life of the light source 101, the temperature control mode selection control unit 114 may select the dew condensation suppression effect with priority over the life of the light source 101 that has already exceeded its life to drive the light source 101 in the dew condensation suppression mode. Therefore, according to the present embodiment, it is possible to provide an illuminating device in which improvement in the dew suppression effect of the light source 101 can be expected as compared to those of the first to third embodiments.

In the above description, as the fifth embodiment, the determination of whether the cumulative drive time exceeds the set value is added to the control flow for suppressing dew condensation in the illuminating device 1 according to the first embodiment. However, the determination of whether the cumulative drive time exceeds the set value may be added to the control flow for suppressing dew condensation in the illuminating device 1 according to the second embodiment or the third embodiment. That is, even when "life exceeded" is selected in addition to "outside air" or "rewriting" for the selection timing of the light source life setting in the priority item setting, the similar advantageous effect can be obtained, and it is therefore included in the fifth embodiment.

Sixth Embodiment

A sixth embodiment of the present invention will be described with reference to FIG. 18. FIG. 18 is a diagram schematically showing an endoscope system 200 according the sixth embodiment, in which the endoscope system 200 includes the illumination device 1 according to any one of the first to fifth embodiments.

The endoscope system 200 includes the illumination device 1 according to any one of the first to fifth embodiments, an endoscope 201, a control device 300, a video processor 30, and a displaying device 40. The endoscope 201 includes a flexible insertion section 202 to be inserted into an insertion target, and a control section 203 provided on the proximal end side of the insertion section 202. The illuminating device 1 includes the optical fibers 102 incorporated in the endoscope 201. The illumination device 1 supplies illumination light emitted from an illumination window (not shown) provided at the distal end of the insertion section 202 of the endoscope 201. The light source device 10, the control device 100, etc. of the illuminating device 1 may be incorporated in the control device 300.

The control device 300 controls various operations of the endoscope 201. Further, the control device 300 causes the displaying device 40 to display the setting content of the priority item setting. The video processor 30 processes an electric signal from an imaging element (not shown) in the distal end of the insertion section 202 of the endoscope 201 to transmit the signal to the displaying device 40. The displaying device 40 displays an endoscopic observation image in the insertion target.

When the temperature control unit 103 is temperature-controlled by the temperature control mode selection control unit 114 in the dew condensation suppression mode, a message 302 is displayed on the displaying device 40. The message 302 is, for example, "Operating in dew condensation suppression mode".

If the temperature control unit 103 is temperature-controlled in the normal operation mode by the temperature control mode selection control unit 114 based on the priority item setting in a state where the dew condensation determination unit 112 determines that dew condensation may occur, the displaying device 40 displays a message 303 warning the possibility of dew condensation. The message 303 is, for example, "Warning. Dew condensation may occur!" It may alternatively read "Warning. Dew condensation may occur! Hurry up!" Along with the display of the message 303, a voice of warning dew condensation occurrence may be generated by a voice generation device (not shown) in the control device 300. The warning voice says, for example, "Dew condensation may occur!" Alternatively, it may say: "Dew condensation may occur. Hurry up!", or may simply comprise a warning sound. The displaying device for displaying a message indicating a warning may be a displaying device or a display unit different from the displaying device 40 on which the endoscopic observation image is displayed, and the voice generation device for generating the warning may be a voice generation device or a speaker different from the control device 300.

In the present embodiment, a message representing a warning is displayed, and this allows the user to recognize that dew condensation may occur in the light source 101 or the temperature control unit 103. In addition, the user can recognize that the work should be urgently conducted so as to minimize the possibility of dew condensation occurrence and the degree of dew condensation in the light source 101 or the temperature control unit 103.

According to the present embodiment, it is possible to provide an illuminating device capable of further reducing the degree of (damage by) the occurrence of dew condensation because the user recognizes that the environment is likely to cause dew condensation.

Seventh Embodiment

A seventh embodiment of the present invention will be described with reference to FIG. 19. FIG. 19 schematically shows a microscope system 400 according to the seventh embodiment, in which the microscope system 400 includes the illumination device 1 according to any one of the first to fifth embodiments.

The illumination device 1 is applicable to not only an endoscope but also a microscope. In the seventh embodiment, in the microscope system 400, the illuminating device 1 of the first to fifth embodiments is used as illumination of the microscope 401. That is, the microscope system 400 is provided with the illuminating device 1 according to any one of the first to fifth embodiments.

A stage 403 is provided on a frame 412 of the microscope 401, and a sample 402 to be observed by the microscope 401 is provided on the stage 403. In the frame 412, light sources 101 configured to form illumination light, in this case, five color light sources 101R, 101B, 101G, 101V, and 101A, are provided on the temperature control units 103 so as to be cooled and heated by the temperature control units 103. The light sources 101 and the temperature control units 103 are parts of the illuminating device 1 according to any one of the first to fifth embodiments. The temperature control units 103 are electrically connected to the temperature control mode selection control unit 114 of the control device 100. The temperature control mode selection control unit 114 temperature-controls the temperature control units 103 based on a desired temperature control mode and priority item setting.

Illumination light 413 emitted from the light sources 101R, 101B, 101G, 101V, and 101A is combined into an optical fiber 411 using an optical coupler or the like (not shown) and then emitted from a fiber output end 409. The emitted illumination light 413 is condensed into an appropriate beam by a condenser lens 410, and then reflected by a mirror 414 toward an objective lens 407, and the illumination light 413 condensed by the objective lens 407 illuminates the sample 402 on the stage 403. Correcting the reflected light of the illumination light 413 applied to the sample 402 through an objective lens 408 allows the user to observe the sample 402.

In the present embodiment, the control flow for suppressing dew condensation in the illuminating device 1 according to any one of the first to fifth embodiments is applicable. That is, if the dew condensation determination unit 112 determines that dew condensation may occur, the temperature control mode selection control unit 114 selects the dew condensation suppression mode as the temperature control mode based on the priority item setting. The temperature control mode selection control unit 114 controls the temperature control unit 103 in the dew condensation suppression mode so that the temperatures of the light source 101 and the temperature control unit 103 become the second target temperature. This suppresses or prevents the occurrence of dew condensation in the light source 101 and the temperature control unit 103.

The light source 101 and the temperature control unit 103 are temperature-controlled based on the priority item setting set in the temperature control mode selection control unit 114. Therefore, for example, if priority is given to special light observation, even when the dew condensation determination unit 112 determines that dew condensation may occur, only the red light source 101R, the green light source 101G, and the blue light source 101B are driven in the dew condensation suppression mode, and the violet light source 101V and the orange light source 101A are driven in the normal operation mode.

According to the present embodiment, the illuminating device 1 of the present invention can be used not only in the endoscope system but also in the microscope system. In particular, when special light observation is applied, a microscope system including the illumination device 1 is effective.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illuminating device comprising:
   a semiconductor light source;
   a temperature control unit that is disposed on the semiconductor light source and configured to control a temperature of the semiconductor light source to a desired temperature;
   a dew condensation determination unit configured to determine whether dew condensation may occur in the illuminating device based on at least one of a temperature associated with the illuminating device and an ambient environment condition of the illuminating device; and
   a temperature control mode selection control unit configured to select, as a temperature control mode of the temperature control unit, a dew condensation suppression mode in which the temperature control unit is caused to have a temperature that is higher than a predetermined temperature and equal to or less than an upper limit of a usable temperature of the semiconductor light source, based on priority items of operational control of the illuminating device and characteristics of the semiconductor light source, to temperature-control the temperature control unit, when the dew condensation determination unit determines that dew condensation may occur.

2. The illuminating device according to claim 1,
   comprising semiconductor light sources including the semiconductor light source and temperature control units including the temperature control unit,
   wherein each of the temperature control units is disposed on each of the semiconductor light sources,
   wherein the priority items include "light source setting" in which a semiconductor light source targeted for temperature control is selected from the semiconductor light sources based on optical characteristics of each of the semiconductor light sources, and
   wherein the temperature control mode selection control unit temperature-controls the temperature control unit based on a temperature control target value of the selected semiconductor light source in the temperature control mode.

3. The illuminating device according to claim 2,
   wherein the "light source setting" is setting relating to a color of each of the semiconductor light sources, and
   wherein the semiconductor light sources include light sources of at least two colors selected from a red light source, a green light source, a blue light source, a violet light source, and an orange light source.

4. The illuminating device according to claim 3,
   wherein light output from the red light source has a center wavelength $\lambda$ of $640 \leq \lambda \leq 760$ nm,
   wherein light output from the green light source has a center wavelength $\lambda$ of $500 \leq \lambda \leq 590$ nm,
   wherein light output from the blue light source has a center wavelength $\lambda$ of $440 \leq \lambda \leq 500$ nm, wherein light output from the violet light source has a center wavelength λ of 380≤λ≤440 nm, and
wherein light output from the orange light source has a center wavelength λ of 590≤λ≤610 nm.

5. The illuminating device according to claim 2,
wherein the temperature control target value includes:
a first target value used in a normal operation mode applied to temperature control of the temperature control unit when the dew condensation determination unit determines that no dew condensation may occur; and
a second target value used in the dew condensation suppression mode applied to temperature control of the temperature control unit when the dew condensation determination unit determines that dew condensation may occur.

6. The illuminating device according to claim 5,
wherein the second target value is higher than the first target value, and is a constant indicating a preset temperature equal to or less than a usable upper limit temperature of each of the semiconductor light sources.

7. The illuminating device according to claim 5,
further comprising an ambient environment temperature sensor configured to detect an ambient environment temperature of the illuminating device,
wherein the second target value is a value of temperature obtained by adding a predetermined correction value to a value of temperature detected by the ambient environment temperature sensor when the dew condensation determination unit determines that dew condensation may occur, and is a variable of temperature equal to or less than the usable upper limit temperature of the semiconductor light source.

8. The illuminating device according to claim 5,
further comprising an ambient environment temperature sensor configured to detect an ambient environment temperature of the illuminating device,
wherein the second target value is a value of temperature obtained by adding a predetermined correction value to a value of temperature detected by the ambient environment temperature sensor when the dew condensation determination unit determines that dew condensation may occur, and is a function of temperature continuously calculated with a predetermined sampling period based on a value of the ambient environment temperature sensor detected with a predetermined sampling period in real time continuously, and equal to or less than the usable upper limit temperature of the semiconductor light source.

9. The illuminating device according to claim 8,
wherein a cycle of detecting an ambient environment temperature by the ambient environment temperature sensor, determining whether dew condensation may occur by the dew condensation determination unit, and selecting the temperature control mode by the temperature control mode selection control unit is repeated, and
wherein, when the dew condensation determination unit determines that dew condensation may occur, the temperature control mode selection control unit rewrites the second target value to cause the storage unit to store the rewritten second target value.

10. The illuminating device according to claim 5,
wherein the second target value is higher than the first target value by 5° C. or more, or higher than a value, by 5° C. or more, of temperature output from an ambient environment temperature sensor configured to detect an ambient environment temperature of the illuminating device.

11. The illuminating device according to claim 5,
wherein the priority items include at least one of "all-color dew condensation suppression setting", "all-color dew condensation suppression disable setting", "light source life setting", "special light observation setting", "new light source setting", and "special use setting".

12. The illuminating device according to claim 11,
wherein, in the all-color dew condensation suppression setting, the temperature control mode selection control unit temperature-controls, in the dew condensation suppression mode, the temperature control units disposed on the semiconductor light sources of all colors included in the illuminating device.

13. The illuminating device according to claim 11,
wherein, in the all-color dew condensation suppression disable setting, the temperature control mode selection control unit temperature-controls, in the normal operation mode, the temperature control units disposed on the semiconductor light sources of all colors included in the illuminating device.

14. The illuminating device according to claim 11,
wherein, in the "light source life setting", the "special light observation setting", the "new light source setting", or the "special use setting", the temperature control mode selection control unit temperature-controls, in the dew condensation suppression mode, the temperature control unit disposed on the semiconductor light source of a color selected in the "light source setting".

15. The illuminating device according to claim 14,
wherein, in the "light source life setting", any one of "always", "outside air", and "rewriting" is set for "selection timing", and setting relating to "cumulative time" and "life exceeded" is possible.

16. The illuminating device according to claim 14,
wherein, in the "special light observation setting", setting relating to any one of "always", "outside air", and "rewriting" is possible for "selection timing".

17. The illuminating device according to claim 15,
wherein, in the "light source lifetime setting" and the "special light observation setting", the temperature control unit disposed on the semiconductor light source for which the "always" is selected is always temperature-controlled in the dew condensation suppression mode in a state where the temperature control mode selection control unit selects the dew condensation suppression mode as the temperature control mode.

18. The illuminating device according to claim 15,
wherein, in the "light source lifetime setting", the temperature control unit disposed on the semiconductor light source for which the "outside air" or the "rewriting" is selected is temperature-controllable in the dew condensation suppression mode only when an upper limit of a drivable temperature of the selected semiconductor light source is higher than the second target value in a state where the temperature control mode selection control unit selects the dew condensation suppression mode as the temperature control mode.

19. The illuminating device according to claim 15,
further comprising a drive time measurement unit configured to measure cumulative drive time of each of the semiconductor light sources,
wherein, in the "light source lifetime setting", the temperature control unit disposed on the semiconductor light source for which the "cumulative time" is selected is temperature-controllable in the dew condensation suppression mode only when the cumulative drive time measured by the drive time measurement unit of the selected semiconductor light source does not exceed a predetermined value in a state where the temperature control mode selection control unit selects the dew condensation suppression mode as the temperature control mode.

20. The illuminating device according to claim 15,
further comprising a drive time measurement unit configured to measure cumulative drive time of each of the semiconductor light sources,
wherein, in the "light source life setting", the temperature control unit disposed on the semiconductor light source for which the "life exceeded" is selected is temperature-controllable in the dew condensation suppression mode only when cumulative drive time measured by the drive time measurement unit of the selected semiconductor light source exceeds an expected life in a state where the temperature control mode selection control unit selects the dew condensation suppression mode as the temperature control mode.

\* \* \* \* \*